(12) United States Patent
Shirley et al.

(10) Patent No.: US 8,637,736 B2
(45) Date of Patent: Jan. 28, 2014

(54) STRESS-RELATED POLYPEPTIDES AND METHODS OF USE IN PLANTS

(75) Inventors: Amber Shirley, Durham, NC (US); Damian Allen, Champaign, IL (US); Ruoying Chen, Duluth, GA (US)

(73) Assignee: BASF Plant Science GmbH (DE)

( * ) Notice: Subject to any disclaimer, the term of this patent is extended or adjusted under 35 U.S.C. 154(b) by 904 days.

(21) Appl. No.: 12/296,460

(22) PCT Filed: Apr. 3, 2007
(Under 37 CFR 1.47)

(86) PCT No.: PCT/EP2007/053219
§ 371 (c)(1),
(2), (4) Date: Jan. 15, 2010

(87) PCT Pub. No.: WO2007/118790
PCT Pub. Date: Oct. 25, 2007

(65) Prior Publication Data
US 2010/0175149 A1    Jul. 8, 2010

Related U.S. Application Data

(60) Provisional application No. 60/744,750, filed on Apr. 13, 2006.

(51) Int. Cl.
*C07H 21/04*    (2006.01)
*C12N 15/82*    (2006.01)

(52) U.S. Cl.
USPC ........ 800/289; 435/320.1; 435/419; 536/23.6

(58) Field of Classification Search
None
See application file for complete search history.

(56) References Cited

FOREIGN PATENT DOCUMENTS

WO    WO 01/45495    *    6/2001

OTHER PUBLICATIONS

Rubio et al. (Physiol. Plant, 109:34-43, 2000).*
Banuelos et al. (Plant Physiol., 130:784-795, 2002).*
Yang et al. Molecular evolution and functional divergence of HAK potassium transporter gene family in rice (*Oryza sativa* L.). Journal of Genetics and Genomics. 2009. 36(3), 161-172.*
Scott et al. The pendred syndrome gene encodes a chloride-iodide transport protien. Nature Genetics. 1999. 21, 440-443.*
Everett et al. Pendred syndrom is casused by mutations in a putative sulphate transporter gene (PDS). Nature Genetics. 1997. 17, 411-422.*
Schaefer et al. Efficient gene targeting in the moss *Physcomitrella patens*. The Plant Journal. 1997. 11(6): 1195-1206.*
Francisco Rubio, Guillermo E. Santa-Maria and Alonso Rodriguez-Navarro, "Cloning of *Arabidopsis* and barley cDNAs encoding HAK potassium transporters in root and shoot cells" Physiologia Plantarum, vol. 109; May 2000, pp. 34-43.
Maria A. Banuelos, Blanca Garciadeblas, Beatriz Cubero and Alonso Rodriguez-Navarro, "Inventory and Functional Characterization of the HAK Potassium Transporters of Rice" Plant Physiology, vol. 130; Oct. 2002, pp. 784-795.
Dietmar Geiger, Dirk Becker, Benoit Lacombe and Rainer Hedrich, "Outer Pore Resides Control the H+ and K+ Sensitivity of the *Arabidopsis* Potassium Channel AKT3" The Plant Cell, vol. 14, Aug. 2002, pp. 1859-1868.
Database EMBL [online] "*Physcomitrella patnes* subsp. patents cDNA clone: pph14e17, 3" end, signle read EMBL: BJ167175, Jan. 22, 2002.
Database EMBL[online] "*Physcomitrella patens* subsp. patens cDNA clone: PPLS120B07, 5' end" EMBL: BY984202, May 24, 2006.

* cited by examiner

*Primary Examiner* — Cathy Kingdon Worley
*Assistant Examiner* — Ashley K Buran
(74) *Attorney, Agent, or Firm* — Patricia A. McDaniels

(57) ABSTRACT

A transgenic plant transformed by a Stress-Related Polypeptide (SRP) coding nucleic acid, wherein expression of the nucleic acid sequence in the plant results in the plant's increased growth under normal or stress conditions and/or increased tolerance to environmental stress as compared to a wild type variety of the plant. Also provided are agricultural products, including seeds, produced by the transgenic plants. Also provided are isolated SRPs, and isolated nucleic acid coding SRPs, and vectors and host cells containing the latter.

22 Claims, 3 Drawing Sheets

Figure 1

| Gene Name | Gene Identifier | Nucleic acid SEQ ID NO: | Protein SEQ ID NO: |
|---|---|---|---|
| PpAKT-3 | EST472 | 1 | 2 |
| GmAKT-2 | GM59666231 | 3 | 4 |
| TaAKT-1 | TA59824966 | 5 | 6 |

Potassium Transporter domain (symbol )

EST 472         from amino acid 78 to 772

TA59824966      from amino acid 82 to 732

GM59666231      from amino acid 43 to 768

STRESS-RELATED POLYPEPTIDES AND METHODS OF USE IN PLANTS

This application is a national stage application under 35 U.S.C. §371 of PCT/EP2007/053219, filed Apr. 3, 2007, which claims benefit of U.S. provisional application No. 60/744,750, filed Apr. 13, 2006. The entire contents of each of the above-identified applications are incorporated herein by reference.

BACKGROUND OF THE INVENTION

1. Field of the Invention

This invention relates generally to nucleic acid sequences encoding polypeptides that are associated with increased growth in plants. In particular, this invention relates to nucleic acid sequences encoding polypeptides that confer upon a plant increased growth under normal or abiotic stress conditions and/or increased tolerance under abiotic stress conditions.

2. Background Art

Abiotic environmental stresses, such as drought stress, salinity stress, heat stress, and cold stress, are major limiting factors of plant growth and productivity. Crop losses and crop yield losses of major crops, such as soybean, rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism, which ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold, and salt tolerance in model drought-, cold-, and/or salt-tolerant plants are complex in nature and involve multiple mechanisms of cellular adaptation and numerous metabolic pathways. This multi-component nature of stress tolerance has not only made breeding for tolerance largely unsuccessful, but also has limited the ability to genetically engineer stress tolerant plants using biotechnological methods.

Drought stresses, heat stresses, cold stresses, and salt stresses, have a common theme important for plant growth, and that is water availability. As discussed above, most plants have evolved strategies to protect themselves against these conditions of desiccation, however, if the severity and duration of the drought conditions are too great, the effects on plant development, growth, and yield of most crop plants are profound. Furthermore, most of the crop plants are very susceptible to higher salt concentrations in the soil. Because high salt content in some soils results in less water being available for cell intake, high salt concentration has an effect on plants similar to the effect of drought on plants. Additionally, under freezing temperatures, plant cells lose water as a result of ice formation that starts in the apoplast and withdraws water from the symplast. A plant's molecular response mechanisms to each of these stress conditions are common, and ion transporters play an essential role in these molecular mechanisms.

Common damage from different stresses such as drought, salinity, and cold stress, appears to be mostly due to dehydration (Smirnoff, 1998, Curr. Opin. Biotech. 9:214-219). Drought (water stress)-tolerant and -sensitive plants can be clearly distinguished by the dramatic accumulation of ions and solutes in tolerant plants that leads to osmotic adjustments (Bohnert and Jensen, 1996, TIBTECH 14:89-97). Drought and high salt conditions may interact with mineral nutrition in a number of ways as a consequence of (1) reduced transport of ions through the soil to the roots; and/or (2) modified uptake of ions by the roots.

Potassium is a major plant macronutrient, and the potassium cation is the most abundant cation in plants. Movement and transport of potassium is important for plant growth, development, osmoregulation, and homeostasis. Potassium transporters in plants have been identified as belonging to several families, including the HAK family. The HAK family contains members with homology to potassium transporters first identified in *Escherichia coli* and *Schwanniomyces occidentalis*. These HAK potassium transporters are found as large gene families in *Arabidopsis* (Maeser et al., 2001) and in rice (Banuelos et al., 2002). Hydrophobicity profiles of this HAK class of potassium transporters suggest that these proteins possess 12 transmembrance domains and a long cytosolic loop. Some members of this family have been demonstrated to function as low-affinity potassium cation transporters (Quintero et al., 1997) while in other organisms the potassium cation transporter has been demonstrated to function as a high-affinity transporter (Rubio et al., 2000).

Potassium is particularly important in plants not only as a nutrient, but also as an osmoticum. Potassium can make a 30-50% contribution to water potential, particularly in older leaf tissues (Munns et al., 1979, Aust. J. Plant Physiol. 6:379-389). After prolonged drought in the field, potassium accumulates in leaves of ryegrass and barley, and could have a role in osmotic adjustment. In addition, potassium plays a key role in the opening of the stomata. Because potassium is lost from the guard cells (Ehret and Boyer, 1979, J. Exper. Bot. 30:225-234), a reduced supply of potassium reduces stomatal conductance to $CO_2$ much more than it reduces internal conductance (Terry and Ulrich, 1973, Plant Physiol. 51:783-786).

Plant roots can absorb potassium over more than a 1000-fold concentration range, and the concentration dependence of potassium uptake by roots has complex kinetics, suggesting the presence of multiple potassium uptake systems. Gene families encoding inward-rectifying K+ channels have been identified in several plant species. The AKT1 K+ channel gene is predominantly expressed in roots and genetic analysis indicates that the AKT1 channel mediates the uptake of K+ in both the micromolar and millimolar ranges (Hirsch et al., 1998, Science 280:918-921). Active transporters also participate in K+ uptake, and several candidate genes encoding energized transporters have been identified (Hirsch and Sussman, 1999, TIBTECH 17:356-361).

Plant biomass is yield for forage crops like alfalfa, silage corn, and hay. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679). In this way a standard environment is used as a proxy for the diverse and dynamic environments encountered at different locations and times by crops in the field.

Harvest index, the ratio of seed yield to above-ground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73) Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water, and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

There is a fundamental physiochemically-constrained trade-off, in all terrestrial, photosynthetic organisms, between carbon dioxide ($CO_2$) absorption and water loss (Taiz and Zeiger, 1991, Plant Physiology, Benjamin/Cummings Publishing Co., p. 94). $CO_2$ needs to be in aqueous solution for the action of $CO_2$ fixation enzymes such as Rubisco (Ribulose 1,5-bisphosphate Carboxylase/Oxygenase) and PEPC (Phosphoenolpyruvate carboxylase). As a wet cell surface is required for $CO_2$ diffusion, evaporation will inevitably occur when the humidity is below 100% (Taiz and Zeiger, 1991, p. 257). Plants have numerous physiological mechanisms to reduce water loss (e.g. waxy cuticles, stomatal closure, leaf hairs, sunken stomatal pits). As these barriers do not discriminate between water and $CO_2$ flux, these water conservation measures will also act to increase resistance to $CO_2$ uptake (Kramer, 1983, Water Relations of Plants, Academic Press p. 305). Photosynthetic $CO_2$ uptake is absolutely required for plant growth and biomass accumulation in photoautotrophic plants.

Water Use Efficiency (WUE) is a parameter frequently used to estimate the trade off between water consumption and $CO_2$ uptake/growth (Kramer, 1983, Water Relations of Plants, Academic Press p. 405). WUE has been defined and measured in multiple ways. One approach is to calculate the ratio of whole plant dry weight, to the weight of water consumed by the plant throughout its life (Chu et al., 1992, Oecologia 89:580). Another variation is to use a shorter time interval when biomass accumulation and water use are measured (Mian et al., 1998, Crop Sci. 38:390). Another approach is to utilize measurements from restricted parts of the plant, for example, measuring only aerial growth and water use (Nienhuis et al 1994 Amer J Bot 81:943). WUE also has been defined as the ratio of $CO_2$ uptake to water vapor loss from a leaf or portion of a leaf, often measured over a very short time period (e.g. seconds/minutes) (Kramer, 1983, p. 406). The ratio of $^{13}C/^{12}C$ fixed in plant tissue, and measured with an isotope ratio mass-spectrometer, also has been used to estimate WUE in plants using $C_3$ photosynthesis (Martin et al., 1999, Crop Sci. 1775).

An increase in WUE is informative about the relatively improved efficiency of growth and water consumption, but this information taken alone does not indicate whether one of these two processes has changed or both have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increased water use (i.e. no change in WUE), could also increase yield. Therefore new methods to increase both WUE and biomass accumulation are required to improve agricultural productivity. As WUE integrates many physiological processes relating to primary metabolism and water use, it is typically a highly polygenic trait with a large genotype by environment interaction (Richards et al., 2002, Crop Sci. 42:111). For these and other reasons, few attempts to select for WUE changes in traditional breeding programs have been successful.

Although some genes that are involved in stress responses and water use efficiency in plants have been characterized, the characterization and cloning of plant genes that confer stress tolerance and water use efficiency remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a need, therefore, to identify additional genes expressed in stress tolerant plants and plants that are efficient in water use that have the capacity to confer stress tolerance and/or increased water use efficiency to the host plant and to other plant species. Newly generated stress tolerant plants and plants with increased water use efficiency will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

SUMMARY OF THE INVENTION

This invention fulfills, in part, the need to identify new unique genes capable of conferring stress tolerance and/or increased growth under normal or stress conditions to plants upon modifying expression of genes. The present invention describes a novel genus of Stress-Related Polypeptides (SRPs) and SRP coding nucleic acids that are important for modulating a plant's growth and response to an environmental stress. More particularly, modifying expression of these SRP coding nucleic acids in a plant results in the plant's increased growth under normal or stress conditions and/or increased tolerance to an environmental stress.

Therefore, the present invention includes an isolated plant cell comprising an SRP coding nucleic acid, wherein expression of the nucleic acid sequence in the plant cell results in increased growth under normal or stress conditions and/or increased tolerance to an environmental stress as compared to a wild type variety of the plant cell. Preferably, the SRP is an Active Potassium Channel Transporter (AKT). More preferably, the AKT is from *Physcomitrella patens, Glycine max*, or *Triticum aestivum*. Namely, described herein are *P. patens* Active Potassium Channel Transporters (PpAKT-3), *Glycine max* Active Potassium Transporters (GmAKT-2), and *Triticum aestivum* Active Potassium Transporter (TaAKT-1).

The invention provides in some embodiments that the SRP and coding nucleic acid are those that are found in members of the genus *Physcomitrella, Glycine*, or *Triticum*. In another preferred embodiment, the nucleic acid and polypeptide are from a *Physcomitrella patens* plant, a *Glycine max* plant, or a *Triticum aestivum* plant. The invention provides that the environmental stress can be salinity, drought, nitrogen, temperature, metal, chemical, pathogenic, and oxidative stresses, or combinations thereof. In preferred embodiments, the environmental stress can be selected from one or more of the group consisting of drought, high salt, and low temperature.

The invention further provides a seed produced by a transgenic plant transformed by an SRP coding nucleic acid, wherein the plant is true breeding for increased growth under normal or stress conditions and/or increased tolerance to an environmental stress as compared to a wild type variety of the plant.

The invention further provides an agricultural product produced by any of the below-described transgenic plants, plant parts, or seeds. The invention further provides an isolated SRP as described below. The invention further provides an isolated SRP coding nucleic acid, wherein the SRP coding nucleic acid codes for an SRP as described below.

The invention further provides an isolated recombinant expression vector comprising an SRP coding nucleic acid as described below, wherein expression of the vector in a host cell results in the plant's increased growth under normal or stress conditions and/or increased tolerance to an environmental stress as compared to a wild type variety of the host cell. The invention further provides a host cell containing the vector and a plant containing the host cell.

The invention further provides a method of producing a transgenic plant with an SRP coding nucleic acid, wherein expression of the nucleic acid in the plant results in the plant's increased growth under normal or stress conditions and/or increased tolerance to an environmental stress as compared to a wild type variety of the plant comprising: (a) transforming a plant cell with an expression vector comprising an SRP coding nucleic acid, and (b) generating from the plant cell a transgenic plant with increased growth under normal or water-limited conditions and/or an increased tolerance to an environmental stress as compared to a wild type variety of the plant. In preferred embodiments, the SRP and SRP coding nucleic acid are as described below.

The present invention further provides a method of identifying a novel SRP, comprising (a) raising a specific antibody response to an SRP, or fragment thereof, as described below; (b) screening putative SRP material with the antibody, wherein specific binding of the antibody to the material indicates the presence of a potentially novel SRP; and (c) identifying from the bound material a novel SRP in comparison to a known SRP. Alternatively, hybridization with nucleic acid probes as described below can be used to identify novel SRP nucleic acids.

The present invention also provides methods of modifying plant growth and/or stress tolerance of a plant comprising, modifying the expression of an SRP nucleic acid in the plant, wherein the SRP is as described below. The invention provides that this method can be performed such that the growth under normal or stress conditions and/or stress tolerance is either increased or decreased. Preferably, growth under normal or stress conditions and/or stress tolerance is increased in a plant via increasing expression of an SRP nucleic acid.

BRIEF DESCRIPTION OF THE DRAWINGS

FIG. 1 shows the correlation between the gene name and the SEQ ID NO in the sequence listing.

DETAILED DESCRIPTION OF THE INVENTION

Figure 2:
FIG. 2 shows the detailed alignment of the disclosed PpAKT-3 (SEQ ID NO:2, EST472), GmAKT-2 (SEQ ID NO:4, GM59666231), and TaAKT-1 (SEQ ID NO:6, TA59824966) amino acid sequences. The alignment was generated using Align X of Vector NTI. Amino acids that are identical across all sequences are indicated with white text and black shading, amino acids that are conserved among sequences are indicated with black text and light gray shading, and amino acids that are similar over some or all of the sequences are indicated with white text and dark grey shading. Potassium Transporter domain is present in: EST 472 from amino acid 78 to 772, TA59824966 from amino acid 82 to 732, GM59666231 from amino acid 43 to 768.
Figure 2:

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as "Stress-Related Polypeptides" (SRPs), in no way limits the functionality of those sequences.

The present invention describes a novel genus of SRPs and SRP coding nucleic acids that are important for modulating a plant's growth under normal or stress conditions and/or for modulating a plant's response to an environmental stress. More particularly, modifying expression of these SRP coding nucleic acids in a plant results in the plant's increased growth under normal or stress conditions and/or increased tolerance to an environmental stress. Representative members of the SRP genus include, but are not limited to, PpAKT-3, GmAKT-2, and TaAKT-1. In a preferred embodiment, all members of the genus are biologically active ion transporters.

Accordingly, the present invention encompasses stress-related polynucleotide and polypeptide sequences and their use for increasing a plant's growth under normal or stress conditions and/or increasing a plant's tolerance to an environmental stress. In one embodiment, the SRP sequence is from a plant, preferably a *Physcomitrella* plant, a *Glycine* plant, or a *Triticum* plant, and more preferably a *Physcomitrella patens* plant, a *Glycine max* plant, or a *Triticum aestivum* plant. In another embodiment, the SRP sequences include PpAKT-3 (SEQ ID NOs:1 and 2), GmAKT-2 (SEQ ID NOs:3 and 4), and TaAKT-1 (SEQ ID NOs:5 and 6). The disclosed amino acid sequences of a *P. patens* AKT, a *G. max* AKT, and a *T. aestivum* AKT have significant percent identity to known active potassium channel transporters are indicated below.

The present invention provides a transgenic plant cell transformed by an SRP coding nucleic acid, wherein modifying expression of the nucleic acid sequence in the plant cell results in increased growth under normal or stress conditions and/or increased tolerance to an environmental stress as compared to a wild type variety of the plant cell. The invention further provides transgenic plant parts and transgenic plants containing the plant cells described herein. Plant parts include, but are not limited to, stems, roots, ovules, stamens, leaves, embryos, meristematic regions, callus tissue, gametophytes, sporophytes, pollen, microspores, and the like. In one embodiment, the transgenic plant is male sterile. Also provided is a plant seed produced by a transgenic plant transformed by an SRP coding nucleic acid, wherein the seed contains the SRP coding nucleic acid, and wherein the plant is true breeding for increased growth under normal or stress conditions and/or increased tolerance to an environmental stress as compared to a wild type variety of the plant. The invention further provides a seed produced by a transgenic plant expressing an SRP, wherein the seed contains the SRP, and wherein the plant is true breeding for increased growth under normal or stress conditions and/or increased tolerance to an environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characteristics that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more SRP DNA sequences introduced into a plant variety. As also used herein, the term "wild type variety" refers to a group of plants that are analyzed for comparative purposes as a control plant, wherein the wild type variety plant is identical to the test plant (plant transformed with a SRP or plant in which expression of the SRP coding nucleic acid has been modified) with the exception that the wild type variety plant has not been transformed with a SRP coding nucleic acid and/or expression of the SRP coding nucleic acid in the wild type variety plant has not been modified.

The present invention describes that the *P. patens* SRPs (PpAKT-3), the *Glycine max* SRPs (GmAKT-2), and the *Triticum aestivum* SRP (TaAKT-1) are useful for increasing a plant's growth under normal or stress conditions and/or increasing a plant's tolerance to an environmental stress. As used herein, the term polypeptide refers to a chain of at least four amino acids joined by peptide bonds. The chain may be linear, branched, circular, or combinations thereof. Accordingly, the present invention provides isolated SRPs selected from the group consisting of PpAKT-3, GmAKT-2, TaAKT-1, and homologs thereof. In preferred embodiments, the SRP is selected from *P. patens* active potassium channel transporter-3 (PpAKT-3) polypeptide as defined in SEQ ID NO:2, *Glycine max* active potassium channel transporter-2 (GmAKT-2) polypeptide as defined in SEQ ID NO:4, *Triticum aestivum* active potassium channel transporter (TaAKT-1) polypeptide as defined in SEQ ID NO:6, and homologs and orthologs thereof. Homologs and orthologs of the amino acid sequences are defined below.

The SRPs of the present invention are preferably produced by recombinant DNA techniques. For example, a nucleic acid molecule encoding the polypeptide is cloned into an expression vector (as described below), the expression vector is introduced into a host cell (as described below), and the SRP is expressed in the host cell. The SRP can then be isolated from the cells by an appropriate purification scheme using standard polypeptide purification techniques. For the purposes of the invention, the term "recombinant polynucleotide" refers to a polynucleotide that has been altered, rearranged or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, an SRP, or peptide thereof, can be synthesized chemically using standard peptide synthesis techniques. Moreover, native SRPs can be isolated from cells (e.g., *P. patens, Glycine max, Triticum aestivum*, or *Brassica napus*), for example, using an anti-SRP antibody, which can be produced by standard techniques utilizing an SRP or fragment thereof.

As used herein, the term "environmental stress" or "stress" refers to sub-optimal conditions associated with salinity, drought, nitrogen, temperature, metal, chemical, pathogenic, and oxidative stresses, or combinations thereof. In preferred embodiments, the environmental stress can be selected from one or more of the group consisting of salinity, drought, or temperature, or combinations thereof, and in particular, can be selected from one or more of the group consisting of high salinity, low water content, or low temperature. It is also to be understood that as used in the specification and in the claims, "a" or "an" can mean one or more, depending upon the context in which it is used. Thus, for example, reference to "a cell" can mean that at least one cell can be utilized. As also used herein, the term "water use efficiency" refers to the amount of organic matter produced by a plant divided by the amount of water used by the plant in producing it, i.e., the dry weight of a plant in relation to the plant's water use. As used herein, the term "dry weight" refers to everything in the plant other than water, and includes, for example, carbohydrates, proteins, oils, and mineral nutrients.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e., sequences located at the 5' and 3' ends of the nucleic acid) in its naturally occurring replicon. For example, a cloned nucleic acid is considered isolated. In various embodiments, the isolated SRP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Physcomitrella patens* cell, a *Glycine max* cell, a *Triticum aestivum* cell, or a *Brassica napus* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:1, SEQ ID NO:3, SEQ ID NO:5, or a portion thereof, can be isolated using standard molecular biology techniques and the sequence information provided herein. For example, a *P. patens* SRP cDNA can be isolated from a *P. patens* library using all or a portion of the sequence disclosed herein. Moreover, a nucleic acid molecule encompassing all or a portion of the sequence of SEQ ID NO:1, SEQ ID NO:3, or SEQ ID NO:5 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1, SEQ ID NO:3, or SEQ ID NO:5. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an SRP nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1, SEQ ID NO:3, or SEQ ID NO:5. These cDNAs may comprise sequences encoding the SRP, (i.e., the "coding region"), as well as 5' untranslated sequences and 3' untranslated sequences. Alternatively, the nucleic acid molecules of the present invention can comprise only the coding region of SEQ ID NO:1, SEQ ID NO:3, or SEQ ID NO:5, or can contain whole genomic fragments isolated from genomic DNA. The present invention also includes SRP coding nucleic acids that encode an SRP as described herein. Preferred is an SRP coding nucleic acid that encodes an SRP selected from the group consisting of PpAKT-3 (SEQ ID NO:2), GmAKT-2 (SEQ ID NO:4), and TaAKT-1 (SEQ ID NO:6).

Moreover, the nucleic acid molecule of the invention can comprise a portion of the coding region of the sequence in SEQ ID NO:1, SEQ ID NO:3, or SEQ ID NO:5, for example, a fragment that can be used as a probe or primer or a fragment encoding a biologically active portion of an SRP. The nucleotide sequences determined from the cloning of the SRP genes from *P. patens, G. max*, and *T. aestivum* allow for the generation of probes and primers designed for use in identifying and/or cloning SRP homologs in other cell types and organisms, as well as SRP homologs from other mosses and related species. The portion of the coding region also can encode a biologically active fragment of an SRP.

As used herein, the term "biologically active portion of" an SRP is intended to include a portion, e.g., a domain/motif, of an SRP that participates in modulation of growth under normal or stress conditions and/or modulation of stress tolerance in a plant, and more preferably, drought tolerance or salt tolerance. For the purposes of the present invention, modulation of plant growth under normal or water-limited conditions and/or stress tolerance refers to at least a 10% increase or decrease in the growth under normal or water-limited conditions and/or at least a 10% increase or decrease in stress tolerance of a transgenic plant comprising an SRP expression cassette (or expression vector) as compared to the growth under normal or water-limited conditions and/or stress tolerance of a control wild type variety of the plant. Methods for quantitating growth under normal or water-limited conditions and/or stress tolerance are provided at least in Examples 8, 13, and 14 below. In a preferred embodiment, the biologically active portion of an SRP increases a plant's growth under normal or water-limited conditions and/or the plant's tolerance to an environmental stress, as compared to a control wild type variety of the plant.

Biologically active portions of an SRP include peptides comprising amino acid sequences derived from the amino acid sequence of an SRP, e.g., an amino acid sequence of SEQ ID NO:2, SEQ ID NO:4, or SEQ ID NO:6, or the amino acid sequence of a polypeptide identical to an SRP, which include fewer amino acids than a full length SRP or the full length polypeptide which is identical to an SRP, and exhibit at least one activity of an SRP. Typically, biologically active portions (e.g., peptides which are, for example, 5, 10, 15, 20, 30, 35, 36, 37, 38, 39, 40, 50, 100, or more amino acids in length) comprise a domain or motif with at least one activity of an SRP. Moreover, other biologically active portions in which other regions of the polypeptide are deleted, can be prepared by recombinant techniques and evaluated for one or more of the activities described herein. As shown in FIG. 2, the potassium transporter domain is present in EST 472 from amino acid 78 to amino acid 772, TA59824966 from amino acid 82 to amino acid 732, GM59666231 from amino acid 43 to amino acid 768.

The invention also provides SRP chimeric or fusion polypeptides. As used herein, an SRP "chimeric polypeptide" or "fusion polypeptide" comprises an SRP operatively linked to a non-SRP. An SRP refers to a polypeptide having an amino acid sequence corresponding to an SRP, whereas a non-SRP refers to a polypeptide having an amino acid sequence corresponding to a polypeptide which is not substantially identical to the SRP, e.g., a polypeptide that is different from the SRP and is derived from the same or a different organism. With respect to the fusion polypeptide, the term "operatively linked" is intended to indicate that the SRP and the non-SRP are fused to each other so that both sequences fulfill the proposed function attributed to the sequence used. The non-SRP can be fused to the N-terminus or C-terminus of the SRP. For example, in one embodiment, the fusion polypeptide is a GST-SRP fusion polypeptide in which the SRP sequences are fused to the C-terminus of the GST sequences. Such fusion polypeptides can facilitate the purification of recombinant SRPs. In another embodiment, the fusion polypeptide is an SRP containing a heterologous signal sequence at its N-terminus. In certain host cells (e.g., mammalian host cells), expression and/or secretion of an SRP can be increased through use of a heterologous signal sequence.

Preferably, an SRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al., 1992, John Wiley & Sons). Moreover, many expression vectors are commercially available that already encode a fusion moiety (e.g., a GST polypeptide). An SRP encoding nucleic acid can be cloned into such an expression vector such that the fusion moiety is linked in-frame to the SRP.

In addition to fragments and fusion polypeptides of the SRPs described herein, the present invention includes homologs and analogs of naturally occurring SRPs and SRP encoding nucleic acids in a plant. "Homologs" are defined herein as two nucleic acids or polypeptides that have similar, or substantially identical, nucleotide or amino acid sequences, respectively. Homologs include allelic variants, orthologs, paralogs, agonists, and antagonists of SRPs as defined hereafter. The term "homolog" further encompasses nucleic acid molecules that differ from one of the nucleotide sequences shown in SEQ ID NO:1, SEQ ID NO:3, or SEQ ID NO:5 (and portions thereof) due to degeneracy of the genetic code and thus encode the same SRP as that encoded by the nucleotide sequences shown in SEQ ID NO:1, SEQ ID NO:3, or SEQ ID NO:5. As used herein, a "naturally occurring" SRP refers to an SRP amino acid sequence that occurs in nature. Preferably, a naturally occurring SRP comprises an amino acid sequence as shown in SEQ ID NO:2, SEQ ID NO:4, or SEQ ID NO:6.

An agonist of the SRP can retain substantially the same, or a subset, of the biological activities of the SRP. An antagonist of the SRP can inhibit one or more of the activities of the naturally occurring form of the SRP. For example, the SRP antagonist can competitively bind to a downstream or upstream member of the cell membrane component metabolic cascade that includes the SRP, or bind to an SRP that mediates transport of compounds across such membranes, thereby preventing translocation from taking place.

Nucleic acid molecules corresponding to natural allelic variants and analogs, orthologs, and paralogs of an SRP cDNA can be isolated based on their identity to the *P. patens, G. max*, or *T. aestivum* SRP nucleic acids described herein using SRP cDNAs, or a portion thereof, as a hybridization probe according to standard hybridization techniques under stringent hybridization conditions. In an alternative embodiment, homologs of the SRP can be identified by screening combinatorial libraries of mutants, e.g., truncation mutants, of the SRP for SRP agonist or antagonist activity. In one embodiment, a variegated library of SRP variants is generated by combinatorial mutagenesis at the nucleic acid level and is encoded by a variegated gene library. A variegated library of SRP variants can be produced by, for example, enzymatically ligating a mixture of synthetic oligonucleotides into gene sequences such that a degenerate set of potential SRP sequences is expressible as individual polypeptides, or alternatively, as a set of larger fusion polypeptides (e.g., for phage display) containing the set of SRP sequences therein. There are a variety of methods that can be used to produce libraries of potential SRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential SRP sequences. Methods for synthesizing degenerate oligonucleotides are known in the art (See, e.g., Narang, 1983, Tetrahedron 39:3; Itakura et al., 1984, Annu. Rev. Biochem. 53:323; Itakura et al., 1984, Science 198:1056; Ike et al., 1983, Nucleic Acid Res. 11:477).

In addition, libraries of fragments of the SRP coding regions can be used to generate a variegated population of SRP fragments for screening and subsequent selection of homologs of an SRP. In one embodiment, a library of coding sequence fragments can be generated by treating a double stranded PCR fragment of an SRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the SRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of SRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify SRP homologs (Arkin and Yourvan, 1992, PNAS 89:7811-7815; Delgrave et al., 1993, Polypeptide Engineering 6(3):327-331). In another embodiment, cell based assays can be exploited to analyze a variegated SRP library, using methods well known in the art. The present invention further provides a method of identifying a novel SRP, comprising (a) raising a specific antibody response to an SRP, or a fragment thereof, as described herein; (b) screening putative SRP material with the antibody, wherein specific binding of the antibody to the material indicates the presence of a potentially novel SRP; and (c) analyzing the bound material in comparison to known SRP, to determine its novelty.

As stated above, the present invention includes SRP and homologs thereof. To determine the percent sequence identity of two amino acid sequences (e.g., one of the sequences of SEQ ID NO:2, SEQ ID NO:4, or SEQ ID NO:6 and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:2, SEQ ID NO:4, or SEQ ID NO:6) is occupied by the same amino acid residue as the corresponding position in the other sequence (e.g., a mutant form of the sequence selected from the polypeptide sequences of SEQ ID NO:2, SEQ ID NO:4, or SEQ ID NO:6), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2, SEQ ID NO:4, or SEQ ID NO:6. In yet another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence encoded by a nucleic acid sequence shown in SEQ ID NO:1, SEQ ID NO:3, or SEQ ID NO:5. In other embodiments, the SRP amino acid homologs have sequence identity over at least 15 contiguous amino acid residues, more preferably at least 25 contiguous amino acid residues, and most preferably at least 35 contiguous amino acid residues of SEQ ID NO:2, SEQ ID NO:4, or SEQ ID NO:6.

In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in SEQ ID NO:1, SEQ ID NO:3, or SEQ ID NO:5, or to a portion comprising at least 60 consecutive nucleotides thereof. The preferable length of sequence comparison for nucleic acids is at least 75 nucleotides, more preferably at least 100 nucleotides, and most preferably the entire length of the coding region. It is even more preferable that the nucleic acid homologs encode proteins having homology with SEQ ID NO:2, SEQ ID NO:4, or SEQ ID NO:6 over the functional domains shown below.

It is further preferred that the isolated nucleic acid homolog of the invention encodes an SRP, or portion thereof, that is at least 90%, more preferably at least 95% identical to an amino acid sequence of SEQ ID NO:2, SEQ ID NO:4, or SEQ ID NO:6, and that functions as a modulator of plant growth and/or an environmental stress response in a plant. In a more preferred embodiment, overexpression of the nucleic acid homolog in a plant increases the plant's growth under normal or stress conditions and/or increases the tolerance of the plant to an environmental stress. In a further preferred embodiment, the nucleic acid homolog encodes an SRP that functions as an ion transporter, more preferably, an active potassium channel transporter.

For the purposes of the invention, the percent sequence identity between two nucleic acid or polypeptide sequences is determined using the Vector NTI 9.0 (PC) software package (Invitrogen, 1600 Faraday Ave., Carlsbad, Calif. 92008). A gap-opening penalty of 15 and a gap extension penalty of 6.66 are used for determining the percent identity of two nucleic acids. A gap-opening penalty of 10 and a gap extension penalty of 0.1 are used for determining the percent identity of two polypeptides. All other parameters are set at the default settings. For purposes of a multiple alignment (Clustal W algorithm), the gap-opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:1, SEQ ID NO:3, or SEQ ID NO:5 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:1, SEQ ID NO:3, or SEQ ID NO:5. In other embodiments, the nucleic acid is at least 30, 50, 100, 250, or more nucleotides in length. Preferably, an isolated nucleic acid homolog of the invention comprises a nucleotide sequence which hybridizes under highly stringent conditions to the nucleotide sequence shown in SEQ ID NO:1, SEQ ID NO:3, or SEQ ID NO:5, and functions as a modulator of growth under normal or stress conditions and/or a modulator for stress tolerance in a plant. In a further preferred embodiment, overexpression of the isolated nucleic acid homolog in a plant increases a plant's growth under normal or stress conditions and/or increases a plant's tolerance to an environmental stress. In an even further preferred embodiment, the isolated nucleic acid homolog encodes an SRP that functions as an ion transporter, more preferably, an active potassium channel transporter.

As used herein with regard to hybridization for DNA to a DNA blot, the term "stringent conditions" refers to hybridization overnight at 60° C. in 10×Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "stringent conditions" refers to hybridization in a 6×SSC solution at 65° C. In another embodiment, "highly stringent conditions" refers to hybridization overnight at 65° C. in 10×Denhart's solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; Current Protocols in Molecular Biology, Chapter 2, Ausubel et al., eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, New York, 1993. Preferably, an isolated nucleic acid molecule of the invention that hybridizes under stringent or highly stringent conditions to a sequence of SEQ ID NO:1, SEQ ID NO:3, or SEQ ID NO:5 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *P. patens* SRP, *G. max* SRP, or *T. aestivum* SRP.

Using the above-described methods, and others known to those of skill in the art, one of ordinary skill in the art can isolate homologs of the SRP comprising amino acid sequence shown in SEQ ID NO:2, SEQ ID NO:4, or SEQ ID NO:6. One subset of these homologs are allelic variants. As used herein, the term "allelic variant" refers to a nucleotide sequence containing polymorphisms that lead to changes in the amino acid sequences of an SRP and that exist within a natural population (e.g., a plant species or variety). Such natural allelic variations can typically result in 1-5% variance in an SRP nucleic acid. Allelic variants can be identified by sequencing the nucleic acid sequence of interest in a number of different plants, which can be readily carried out by using hybridization probes to identify the same SRP genetic locus in those plants. Any and all such nucleic acid variations and resulting amino acid polymorphisms or variations in an SRP that are the result of natural allelic variation and that do not alter the functional activity of an SRP, are intended to be within the scope of the invention.

Moreover, nucleic acid molecules encoding SRPs from the same or other species such as SRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov et al., 1997, Science 278(5338): 631-637). Analogs, orthologs, and paralogs of a naturally occurring SRP can differ from the naturally occurring SRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably 85-90% or 90-95%, and most preferably 95%, 96%, 97%, 98%, or even 99% identity, or 100% sequence identity, with all or part of a naturally occurring SRP amino acid sequence, and will exhibit a function similar to an SRP. Preferably, an SRP ortholog of the present invention functions as a modulator of plant growth and/or an environmental stress response in a plant and/or functions as an ion transporter. More preferably, an SRP ortholog increases the plant's growth under normal or stress conditions and/or increases the stress tolerance of a plant. In one embodiment, the SRP orthologs maintain the ability to participate in the metabolism of compounds necessary for the construction of cellular membranes in a plant, or in the transport of molecules across these membranes.

In addition to naturally-occurring variants of an SRP sequence that may exist in the population, the skilled artisan will further appreciate that changes can be introduced by mutation into a nucleotide sequence of SEQ ID NO:1, SEQ ID NO:3, or SEQ ID NO:5, thereby leading to changes in the amino acid sequence of the encoded SRP, without altering the functional activity of the SRP. For example, nucleotide substitutions leading to amino acid substitutions at "non-essential" amino acid residues can be made in a sequence of SEQ ID NO:1, SEQ ID NO:3, or SEQ ID NO:5. A "non-essential" amino acid residue is a residue that can be altered from the wild-type sequence of one of the SRPs without altering the activity of said SRP, whereas an "essential" amino acid residue is required for SRP activity. Other amino acid residues, however, (e.g., those that are not conserved or only semi-conserved in the domain having SRP activity) may not be essential for activity and thus are likely to be amenable to alteration without altering SRP activity.

Accordingly, another aspect of the invention pertains to nucleic acid molecules encoding SRPs that contain changes in amino acid residues that are not essential for SRP activity. Such SRPs differ in amino acid sequence from a sequence contained in SEQ ID NO:2, SEQ ID NO:4, or SEQ ID NO:6, yet retain at least one of the SRP activities described herein. In one embodiment, the isolated nucleic acid molecule comprises a nucleotide sequence encoding a polypeptide, wherein the polypeptide comprises an amino acid sequence at least about 50% identical to an amino acid sequence of SEQ ID NO:2, SEQ ID NO:4, or SEQ ID NO:6. Preferably, the polypeptide encoded by the nucleic acid molecule is at least about 50-60% identical to an amino acid sequence of SEQ ID NO:2, SEQ ID NO:4, or SEQ ID NO:6, more preferably at least about 60-70% identical to an amino acid sequence of SEQ ID NO:2, SEQ ID NO:4, or SEQ ID NO:6, even more preferably at least about 70-75%, 75-80%, 80-85%, 85-90%, or 90-95% identical to an amino acid sequence of SEQ ID NO:2, SEQ ID NO:4, or SEQ ID NO:6, and most preferably at least about 96%, 97%, 98%, or 99% identical to an amino acid sequence of SEQ ID NO:2, SEQ ID NO:4, or SEQ ID NO:6. The preferred SRP homologs of the present invention preferably participate in a plant's growth and/or a stress tolerance response, or more particularly, function as an ion transporter, preferably, as an active potassium channel transporter.

An isolated nucleic acid molecule encoding an SRP having sequence identity with a polypeptide sequence of SEQ ID NO:2, SEQ ID NO:4, or SEQ ID NO:6 can be created by introducing one or more nucleotide substitutions, additions, or deletions into a nucleotide sequence of SEQ ID NO:1, SEQ ID NO:3, or SEQ ID NO:5, respectively, such that one or more amino acid substitutions, additions, or deletions are introduced into the encoded polypeptide. Mutations can be introduced into the sequence of SEQ ID NO:1, SEQ ID NO:3, or SEQ ID NO:5 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in an SRP is preferably replaced with another amino acid residue from the same side chain family. Alternatively, in another embodiment, mutations can be introduced randomly along all or part of an SRP coding sequence, such as by saturation mutagenesis, and the resultant mutants can be screened for an SRP activity described herein to identify mutants that retain SRP activity. Following mutagenesis of the sequence of SEQ ID NO:1, SEQ ID NO:3, or SEQ ID NO:5, the encoded polypeptide can be expressed recombinantly and the activity of the polypeptide can be determined by analyzing the transgenic plant's stress tolerance or growth under normal or water-limited conditions, for example, as described in Example 8.

Additionally, optimized SRP nucleic acids can be created. Preferably, an optimized SRP nucleic acid encodes an SRP that binds to a phosphate group and/or modulates a plant's growth under normal or stress conditions and/or tolerance to an environmental stress, and more preferably increases a plant's growth under normal or stress conditions and/or tolerance to an environmental stress upon its overexpression in the plant. As used herein, "optimized" refers to a nucleic acid that is genetically engineered to increase its expression in a given plant or animal. To provide plant optimized SRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence; or 4) to eliminate sequences that cause destabilization, inappropriate polyadenylation, degradation and termination of RNA, or that form secondary structure hairpins or RNA splice sites. Increased expression of SRP nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88:3324-3328; and Murray et al., 1989, Nucleic Acids Res. 17:477-498.

An SRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots, whereas the XTA codon is avoided in both monocots and dicots. Optimized SRP nucleic acids of this invention also preferably have CG and TA doublet avoidance indices closely approximating those of the chosen host plant (e.g., *P. patens*, *G. max*, or *T. aestivum*). More preferably, these indices deviate from that of the host by no more than about 10-15%.

In addition to the nucleic acid molecules encoding the SRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:2, SEQ ID NO:4, or SEQ ID NO:6.

The antisense nucleic acid can be complementary to an entire SRP coding strand, or to only a portion thereof. In one embodiment, an antisense nucleic acid molecule is antisense to a "coding region" of the coding strand of a nucleotide sequence encoding an SRP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding an SRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of SRP mRNA, but more preferably is an oligonucleotide, which is antisense to only a portion of the coding or noncoding region of SRP mRNA. For example, the antisense oligonucleotide can be complementary to the region surrounding the translation start site of the SRP mRNA. An antisense oligonucleotide can be, for example, about 5, 10, 15, 20, 25, 30, 35, 40, 45 or 50 nucleotides in length. Typically, the antisense molecules of the present invention comprise an RNA having 60-100% sequence identity with at least 14 consecutive nucleotides of SEQ ID NO:1, SEQ ID NO:3, or SEQ ID NO:5, or a polynucleotide encoding a polypeptide of SEQ ID NO:2, SEQ ID NO:4, or SEQ ID NO:6. Preferably, the sequence identity will be at least 70%, more preferably at least 75%, 80%, 85%, 90%, 95%, or 98%, and most preferably 99%.

The antisense nucleic acid molecules of the invention are typically administered to a cell or generated in situ such that they hybridize with or bind to cellular mRNA and/or genomic DNA encoding an SRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule also can be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of an SRP polypeptide. As used herein, the term "ribozyme" refers to a catalytic RNA-based enzyme with ribonuclease activity that is capable of cleaving a single-stranded nucleic acid, such as an mRNA, to which it has a complementary region. Ribozymes (e.g., hammerhead ribozymes described in Haselhoff and Gerlach, 1988, Nature 334:585-591) can be used to catalytically cleave SRP mRNA transcripts to thereby inhibit translation of SRP mRNA. A ribozyme having specificity for an SRP-encoding nucleic acid can be designed based upon the nucleotide sequence of an SRP cDNA, as disclosed herein (i.e., SEQ ID NO:1, SEQ ID NO:3, or SEQ ID NO:5) or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in an SRP-encoding mRNA (See, e.g., U.S. Pat. Nos. 4,987,071 and 5,116,742 to Cech et al). Alternatively, SRP mRNA can be used to select a catalytic RNA having a specific ribonuclease activity from a pool of RNA molecules (See, e.g., Bartel and Szostak, 1993, Science 261: 1411-1418). In preferred embodiments, the ribozyme will contain a portion having at least 7, 8, 9, 10, 12, 14, 16, 18, or 20 nucleotides, and more preferably 7 or 8 nucleotides, that have 100% complementarity to a portion of the target RNA. Methods for making ribozymes are known to those skilled in the art (See, e.g., U.S. Pat. Nos. 6,025,167; 5,773,260; and 5,496,698).

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:2, SEQ ID NO:4, or SEQ ID NO:6, or a polypeptide having at least 80% sequence identity with a polypeptide of SEQ ID NO:2, SEQ ID NO:4, or SEQ ID NO:6. The hybridizing RNAs may be substantially or completely complementary. By "substantially complementary," it is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides, ribonucleotide analogs, such as 2'-O-methyl ribosyl residues, or combinations thereof (See, e.g., U.S. Pat. Nos. 4,130,641 and 4,024,222). A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture (See, e.g., U.S. Pat. No. 5,795,715). In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238: 645-650 and Cooney et al., 1988, Science 241: 456-459) and co-suppression (Napoli et al., 1990, The Plant Cell 2: 279-289) are known in the art. Partial and full-length cDNAs have been used for the co-suppression of endogenous plant genes (See, e.g., U.S. Pat. Nos. 4,801,340, 5,034,323, 5,231,020, and 5,283,184; Van der Kroll et al., 1990, The Plant Cell 2: 291-299; Smith et al., 1990, Mol. Gen. Genetics 224: 477-481 and Napoli et al., 1990, The Plant Cell 2: 279-289).

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95%, or more. The introduced sense polynucleotide need not be full length relative to the target gene or transcript. Preferably, the sense polynucleotide will have at least 65% sequence identity with at least 100 consecutive nucleotides of SEQ ID NO:1, SEQ ID NO:3, or SEQ ID NO:5. The regions of identity can comprise introns and/or exons and untranslated regions. The introduced sense polynucleotide may be present in the plant cell transiently, or may be stably integrated into a plant chromosome or extrachromosomal replicon.

Alternatively, SRP gene expression can be inhibited by targeting nucleotide sequences complementary to the regulatory region of an SRP nucleotide sequence (e.g., an SRP promoter and/or enhancer) to form triple helical structures that prevent transcription of an SRP gene in target cells (See generally, Helene, 1991, Anticancer Drug Des. 6(6): 569-84; Helene et al., 1992, Ann. N.Y. Acad. Sci. 660: 27-36; and Maher, 1992, Bioassays 14(12): 807-15).

In addition to the SRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of the sequence set forth in SEQ ID NO:1, SEQ ID NO:3, or SEQ ID NO:5; an anti-sense sequence of the sequence set forth in SEQ ID NO:1, SEQ ID NO:3, or SEQ ID NO:5; or naturally occurring mutants thereof. Primers based on a nucleotide sequence of SEQ ID NO:1, SEQ ID NO:3, or SEQ ID NO:5 can be used in PCR reactions to clone SRP homologs. Probes based on the SRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an SRP, such as by measuring a level of an SRP-encoding nucleic acid, in a sample of cells, e.g., detecting SRP mRNA levels or determining whether a genomic SRP gene has been mutated or deleted.

In particular, a useful method to ascertain the level of transcription of the gene (an indicator of the amount of mRNA available for translation to the gene product) is to perform a Northern blot (For reference, see, for example, Ausubel et al., 1988, Current Protocols in Molecular Biology, Wiley: New York). The information from a Northern blot at least partially demonstrates the degree of transcription of the transformed gene. Total cellular RNA can be prepared from cells, tissues or organs by several methods, all well-known in the art, such as that described in Bormann et al., 1992, Mol. Microbiol. 6: 317-326. To assess the presence or relative quantity of polypeptide translated from this mRNA, standard techniques, such as a Western blot, may be employed. These techniques are well known to one of ordinary skill in the art (See, for example, Ausubel et al., 1988, Current Protocols in Molecular Biology, Wiley: New York).

The invention further provides an isolated recombinant expression vector comprising an SRP nucleic acid as described above, wherein expression of the vector in a host cell results in the plant's increased growth under normal or water-limited conditions and/or increased tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., SRPs, mutant forms of SRPs, fusion polypeptides, etc.).

The recombinant expression vectors of the invention can be designed for expression of SRPs in prokaryotic or eukaryotic cells. For example, SRP genes can be expressed in bacterial cells such as *C. glutamicum*, insect cells (using baculovirus expression vectors), yeast and other fungal cells (See Romanos et al., 1992, Foreign gene expression in yeast: a review, Yeast 8: 423-488; van den Hondel et al., 1991, Heterologous gene expression in filamentous fungi, in: More Gene Manipulations in Fungi, J. W. Bennet & L. L. Lasure, eds., p. 396-428: Academic Press: San Diego; and van den Hondelm and Punt, 1991, Gene transfer systems and vector development for filamentous fungi, in: Applied Molecular Genetics of Fungi, Peberdy et al., eds., p. 1-28, Cambridge University Press: Cambridge), algae (Falciatore et al., 1999, Marine Biotechnology 1(3): 239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in PCT Application No. WO 98/01572, and multicellular plant cells (See Schmidt and Willmitzer, 1988, High efficiency *Agrobacterium tumefaciens*-mediated transformation of *Arabidopsis thaliana* leaf and cotyledon explants, Plant Cell Rep. 583-

586; Plant Molecular Biology and Biotechnology, C Press, Boca Raton, Fla., chapter 6/7, S.71-119, 1993; F. F. White, B. Jenes et al., Techniques for Gene Transfer, in: Transgenic Plants, Vol. 1, Engineering and Utilization, eds. Kung and R. Wu, 128-43, Academic Press: 1993; Potrykus, 1991, Annu. Rev. Plant Physiol. Plant Molec. Biol. 42: 205-225 and references cited therein), or mammalian cells. Suitable host cells are discussed further in Goeddel, Gene Expression Technology: Methods in Enzymology 185, Academic Press: San Diego, Calif., 1990. Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith and Johnson, 1988, Gene 67: 31-40), pMAL (New England Biolabs, Beverly, Mass.) and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the SRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant SRP unfused to GST can be recovered by cleavage of the fusion polypeptide with thrombin.

Examples of suitable inducible non-fusion E. coli expression vectors include pTrc (Amann et al., 1988, Gene 69: 301-315) and pET 11d (Studier et al., 1990, Gene Expression Technology: Methods in Enzymology 185, Academic Press, San Diego, Calif., 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, 1990, Gene Expression Technology: Methods in Enzymology 185, Academic Press, San Diego, Calif., 119-128). Another strategy is to alter the sequence of the nucleic acid to be inserted into an expression vector so that the individual codons for each amino acid are those preferentially utilized in the bacterium chosen for expression, such as C. glutamicum (Wada et al., 1992, Nucleic Acids Res. 20: 2111-2118). Such alteration of nucleic acid sequences of the invention can be carried out by standard DNA synthesis techniques.

In another embodiment, the SRP expression vector is a yeast expression vector. Examples of vectors for expression in yeast S. cerevisiae include pYepSec1 (Baldari, et al., 1987, EMBO J. 6: 229-234), pMFa (Kurjan and Herskowitz, 1982, Cell 30: 933-943), pJRY88 (Schultz et al., 1987, Gene 54: 113-123), and pYES2 (Invitrogen Corporation, San Diego, Calif.). Vectors and methods for the construction of vectors appropriate for use in other fungi, such as the filamentous fungi, include those detailed in: van den Hondel and Punt, 1991, "Gene transfer systems and vector development for filamentous fungi," in: Applied Molecular Genetics of Fungi, Peberdy, et al., eds., p. 1-28, Cambridge University Press: Cambridge.

In a preferred embodiment of the present invention, the SRPs are expressed in plants and plants cells such as unicellular plant cells (e.g. algae) (See Falciatore et al., 1999, Marine Biotechnology 1(3): 239-251 and references therein) and plant cells from higher plants (e.g., the spermatophytes, such as crop plants). An SRP may be "introduced" into a plant cell by any means, including transfection, transformation or transduction, electroporation, particle bombardment, agroinfection, and the like. One transformation method known to those of skill in the art is the dipping of a flowering plant into an Agrobacteria solution, wherein the Agrobacteria contain the SRP nucleic acid, followed by breeding of the transformed gametes.

Other suitable methods for transforming or transfecting host cells including plant cells can be found in Sambrook, et al., Molecular Cloning: A Laboratory Manual. Latest ed., Cold Spring Harbor Laboratory, Cold Spring Harbor Laboratory Press, Cold Spring Harbor, N.Y., 1989, and other laboratory manuals such as Methods in Molecular Biology, 1995, Vol. 44, Agrobacterium protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed, canola, manihot, pepper, sunflower, tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of an SRP into a plant is achieved by Agrobacterium mediated gene transfer. Agrobacterium mediated plant transformation can be performed using for example the GV3101(pMP90) (Koncz and Schell, 1986, Mol. Gen. Genet. 204: 383-396) or LBA4404 (Clontech) Agrobacterium tumefaciens strain. Transformation can be performed by standard transformation and regeneration techniques (Deblaere et al., 1994, Nucl. Acids Res. 13: 4777-4788; Gelvin, Stanton, Schilperoort, and Robert, Plant Molecular Biology Manual, $2^{nd}$ Ed.—Dordrecht: Kluwer Academic Publ., 1995, in Sect., Ringbuc Zentrale Signatur: BT11-P ISBN 0-7923-2731-4; Glick, Bernard, Thompson, and John, Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8: 238-242; De Block et al., 1989, Plant Physiol. 91: 694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake or via the silicon carbide fiber technique. (See, for example, Freeling and Walbot "The Maize Handbook" Springer Verlag: New York, 1993, ISBN 3-540-97826-7). A specific example of maize transformation is found in U.S. Pat. No. 5,990,387, and a specific example of wheat transformation can be found in PCT Application No. WO 93/07256.

According to the present invention, the introduced SRP may be maintained in the plant cell stably if it is incorporated into a non-chromosomal autonomous replicon or integrated into the plant chromosomes. Alternatively, the introduced SRP may be present on an extra-chromosomal non-replicating vector and may be transiently expressed or transiently active.

In one embodiment, a homologous recombinant microorganism can be created wherein the SRP is integrated into a chromosome, a vector is prepared which contains at least a portion of an SRP gene into which a deletion, addition, or substitution has been introduced to thereby alter, e.g., functionally disrupt, the SRP gene. Preferably, the SRP gene is a *P. patens, G. max, T. aestivum*, or *B. napus* SRP gene, but it can be a homolog from a related plant or even from a mammalian, yeast, or insect source. In one embodiment, the vector is designed such that, upon homologous recombination, the endogenous SRP gene is functionally disrupted (i.e., no longer encodes a functional polypeptide; also referred to as a knock-out vector). Alternatively, the vector can be designed such that, upon homologous recombination, the endogenous SRP gene is mutated or otherwise altered but still encodes a functional polypeptide (e.g., the upstream regulatory region can be altered to thereby alter the expression of the endogenous SRP). To create a point mutation via homologous recombination, DNA-RNA hybrids can be used in a technique known as chimeraplasty (Cole-Strauss et al., 1999, Nucleic Acids Research 27(5): 1323-1330 and Kmiec, 1999, Gene Therapy American Scientist, 87(3): 240-247). Homologous recombination procedures in *P. patens, G. max, T. aestivum*, or *B. napus* are also well known in the art and are contemplated for use herein.

Whereas in the homologous recombination vector, the altered portion of the SRP gene is flanked at its 5' and 3' ends by an additional nucleic acid molecule of the SRP gene to allow for homologous recombination to occur between the exogenous SRP gene carried by the vector and an endogenous SRP gene, in a microorganism or plant. The additional flanking SRP nucleic acid molecule is of sufficient length for successful homologous recombination with the endogenous gene. Typically, several hundreds of base pairs up to kilobases of flanking DNA (both at the 5' and 3' ends) are included in the vector (See, e.g., Thomas and Capecchi, 1987, Cell 51: 503 for a description of homologous recombination vectors or Strepp et al., 1998, PNAS, 95 (8): 4368-4373 for cDNA based recombination in *P. patens*). The vector is introduced into a microorganism or plant cell (e.g., via polyethylene glycol mediated DNA), and cells in which the introduced SRP gene has homologously recombined with the endogenous SRP gene are selected using art-known techniques.

In another embodiment, recombinant microorganisms can be produced that contain selected systems that allow for regulated expression of the introduced gene. For example, inclusion of an SRP gene on a vector placing it under control of the lac operon permits expression of the SRP gene only in the presence of IPTG. Such regulatory systems are well known in the art.

Whether present in an extra-chromosomal non-replicating vector or a vector that is integrated into a chromosome, the SRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3: 835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5"-untranslated leader sequence from tobacco mosaic virus enhancing the polypeptide per RNA ratio (Gallie et al., 1987, Nucl. Acids Research 15: 8693-8711). Examples of plant expression vectors include those detailed in: Becker, Kemper, Schell, and Masterson, 1992, New plant binary vectors with selectable markers located proximal to the left border, Plant Mol. Biol. 20: 1195-1197; and Bevan, 1984, Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and Wu, Academic Press, 1993, S. 15-38.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35 S promoters (Odell et al., 1985, Nature 313: 810-812), the sX CaMV 35S promoter (Kay et al., 1987, Science 236: 1299-1302) the Sep1 promoter, the rice actin promoter (McElroy et al., 1990, Plant Cell 2: 163-171), the *Arabidopsis* actin promoter, the ubiquitan promoter (Christensen et al., 1989, Plant Molec. Biol. 18: 675-689), pEmu (Last et al., 1991, Theor. Appl. Genet. 81: 581-588), the figwort mosaic virus 35S promoter, the Smas promoter (Velten et al., 1984, EMBO J. 3: 2723-2730), the GRP1-8 promoter, the super promoter (U.S. Pat. No. 5,955,646), the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For a review, see Gatz 1997, Annu. Rev. Plant Physiol. Plant Mol. Biol. 48: 89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2: 397-404), and an ethanol inducible promoter (PCT Application No. WO 93/21334).

In one preferred embodiment of the present invention, the inducible promoter is a stress-inducible promoter. For the purposes of the invention, stress inducible promoters are preferentially active under one or more of the following stresses: sub-optimal conditions associated with salinity, drought, temperature, mental, chemical, pathogenic, and oxidative stresses. Stress inducible promoters include, but are not limited to, Cor78 (Chak et al., 2000, Planta 210: 875-883; Hovath et al., 1993, Plant Physiol. 103: 1047-1053), Cor15a (Artus et al., 1996, PNAS 93(23): 13404-09), Rci2A (Medina et al., 2001, Plant Physiol. 125: 1655-66; Nylander et al., 2001, Plant Mol. Biol. 45: 341-52; Navarre and Goffeau, 2000, EMBO J. 19: 2515-24; Capel et al., 1997, Plant Physiol. 115: 569-76), Rd22 (Xiong et al., 2001, Plant Cell 13: 2063-83; Abe et al., 1997, Plant Cell 9: 1859-68; Iwasaki et al., 1995, Mol. Gen. Genet. 247: 391-8), cDet6 (Lang and Palve, 1992, Plant Mol. Biol. 20: 951-62), ADH1 (Hoeren et al., 1998, Genetics 149: 479-90), KAT1 (Nakamura et al., 1995, Plant Physiol. 109: 371-4), KST1 (Müller-Röber et al., 1995, EMBO 14: 2409-16), Rha1 (Terryn et al., 1993, Plant Cell 5: 1761-9; Terryn et al., 1992, FEBS Lett. 299(3): 287-90), ARSK1 (Atkinson et al., 1997, GenBank Accession # L22302, and PCT Application No. WO 97/20057), PtxA (Plesch et al., GenBank Accession # X67427), SbHRGP3 (Ahn et al., 1996, Plant Cell 8: 1477-90), GH3 (Liu et al., 1994, Plant Cell 6: 645-57), the pathogen inducible PRP1-gene promoter (Ward et al., 1993, Plant. Mol. Biol. 22: 361-366), the heat inducible hsp80-promoter from tomato (U.S. Pat. No. 5,187, 267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm-preferred, and seed coat-preferred (See Thompson et al., 1989, BioEssays 10:108). Examples of seed-preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol. Gen. Genet. 225(3): 459-67), the oleosin-promoter from *Arabidopsis* (PCT Application No. WO 98/45461), the phaseolin-promoter from *Phaseolus vulgaris* (U.S. Pat. No. 5,504,200), the Bce-4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the γ-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43: 729-736).

The invention further provides a recombinant expression vector comprising an SRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to an SRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1(1), and Mol et al., 1990, FEBS Letters 268: 427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an SRP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

A host cell of the invention, such as a prokaryotic or eukaryotic host cell in culture, can be used to produce (i.e., express) an SRP. Accordingly, the invention further provides methods for producing an SRP using the host cells of the invention. In one embodiment, the method comprises culturing the host cell of invention (into which a recombinant expression vector encoding an SRP has been introduced, or into which genome has been introduced a gene encoding a wild-type or altered SRP) in a suitable medium until the SRP is produced. In another embodiment, the method further comprises isolating an SRP from the medium or the host cell.

Another aspect of the invention pertains to an isolated SRP, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of an SRP in which the polypeptide is separated from some of the cellular components of the cells in which it is naturally or recombinantly produced. In one embodiment, the language "substantially free of cellular material" includes preparations of an SRP having less than about 30% (by dry weight) of non-SRP material (also referred to herein as a "contaminating polypeptide"), more preferably less than about 20% of non-SRP material, still more preferably less than about 10% of non-SRP material, and most preferably less than about 5% non-SRP material.

When the SRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of SRP in which the polypeptide is separated from chemical precursors or other chemicals that are involved in the synthesis of the polypeptide. In one embodiment, the language "substantially free of chemical precursors or other chemicals" includes preparations of an SRP having less than about 30% (by dry weight) of chemical precursors or non-SRP chemicals, more preferably less than about 20% chemical precursors or non-SRP chemicals, still more preferably less than about 10% chemical precursors or non-SRP chemicals, and most preferably less than about 5% chemical precursors or non-SRP chemicals. In preferred embodiments, isolated polypeptides, or biologically active portions thereof, lack contaminating polypeptides from the same organism from which the SRP is derived. Typically, such polypeptides are produced by recombinant expression of, for example, a *P. patens, G. max*, or *T. aestivum* SRP in plants other than *P. patens, G. max*, or *T. aestivum*, or microorganisms such as *C. glutamicum*, ciliates, algae, or fungi.

The nucleic acid molecules, polypeptides, polypeptide homologs, fusion polypeptides, primers, vectors, and host cells described herein can be used in one or more of the following methods: identification of *P. patens, G. max*, or *T. aestivum* and related organisms; mapping of genomes of organisms related to *P. patens, G. max*, or *T. aestivum*; identification and localization of *P. patens, G. max*, or *T. aestivum* sequences of interest; evolutionary studies; determination of SRP regions required for function; modulation of an SRP activity; modulation of the metabolism of one or more cell functions; modulation of the transmembrane transport of one or more compounds; modulation of growth under water-limited conditions; modulation of stress resistance; and modulation of expression of SRP nucleic acids.

The moss *P. patens* is related to other mosses such as Ceratodon purpureus that are capable of growth in the absence of light. Mosses like Ceratodon and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The SRP nucleic acid molecules of the invention have a variety of uses. Most importantly, the nucleic acid and amino acid sequences of the present invention can be used to transform plants, thereby increasing plant growth and/or inducing tolerance to stresses such as drought, high salinity, and cold. The present invention therefore provides a transgenic plant transformed by an SRP nucleic acid, wherein expression of the nucleic acid sequence in the plant results in the plant's increased growth under normal or stress conditions and/or tolerance to an environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, *manihot*, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops, for example.

In particular, the present invention describes using the expression of PpAKT-3 of *P. patens*; GmAKT-2 of *G. max*, and TaAKT-1 of *T. aestivum* to engineer drought-tolerant, salt-tolerant, and/or cold-tolerant plants, and/or plants with increased growth under normal or stress conditions. This strategy has herein been demonstrated for *A. thaliana*, but its application is not restricted to this plant. Accordingly, the invention provides a transgenic plant containing an SRP such as the PpAKT-3 as defined in SEQ ID NO:2, GmAKT-2 as defined in SEQ ID NO:4, or TaAKT-1 as defined in SEQ ID NO:6, wherein the plant has increased growth under normal or stress conditions and/or an increased tolerance to an environmental stress selected from one or more of the group consisting of drought, increased salt, or decreased or increased temperature. In preferred embodiments, the environmental stress is drought or decreased temperature.

Accordingly, the invention provides a method of producing a transgenic plant with an SRP coding nucleic acid, wherein expression of the nucleic acid(s) in the plant results in the plant's increased growth under normal or water-limited conditions and/or increased tolerance to an environmental stress as compared to a wild type variety of the plant comprising: (a) introducing into a plant cell an expression vector comprising an SRP nucleic acid, and (b) generating from the plant cell a transgenic plant with increased growth under normal or water-limited conditions and/or increased tolerance to environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant SRP polynucleotide. In many cases, all or part of the recombinant polynucleotide is stably integrated into a chromosome or stable extra-chromosomal element, so that it is passed on to successive generations. In preferred embodiments, the SRP nucleic acid encodes the polypeptide of SEQ ID NO:2, SEQ ID NO:4, or SEQ ID NO:6.

The present invention also provides a method of modulating a plant's growth under normal or stress conditions and/or modulating a plant's tolerance to an environmental stress comprising, modifying the expression of an SRP coding nucleic acid in the plant. The plant's growth under normal or stress conditions and/or tolerance to the environmental stress can be increased or decreased as achieved by increasing or decreasing the expression of an SRP, respectively. Preferably, the plant's growth under normal or stress conditions and/or tolerance to the environmental stress is increased by increasing expression of an SRP. Expression of an SRP can be modified by any method known to those of skill in the art. The methods of increasing expression of SRPs can be used wherein the plant is either transgenic or not transgenic. In cases where the plant is transgenic, the plant can be transformed with a vector containing any of the above described SRP coding nucleic acids, or the plant can be transformed with a promoter that directs expression of a native SRP in the plant, for example. The invention provides that such a promoter can be tissue preferred, developmentally regulated, stress-inducible, or a combination thereof. Alternatively, non-transgenic plants can have native SRP expression modified by inducing a native promoter. The expression of PpAKT-3 as defined in SEQ ID NO:1, GmAKT-2 as defined in SEQ ID NO:3, or TaAKT-1 as defined in SEQ ID NO:5 in target plants can be accomplished by, but is not limited to, one of the following examples: (a) constitutive promoter, (b) stress-inducible promoter, (c) chemical-induced promoter, and (d) engineered promoter overexpression with, for example, zinc-finger derived transcription factors (Greisman and Pabo, 1997, Science 275: 657).

In a preferred embodiment, transcription of the SRP is modulated using zinc-finger derived transcription factors (ZFPs) as described in Greisman and Pabo, 1997, Science 275: 657 and manufactured by Sangamo Biosciences, Inc. These ZFPs comprise both a DNA recognition domain and a functional domain that causes activation or repression of a target nucleic acid such as an SRP nucleic acid. Therefore, activating and repressing ZFPs can be created that specifically recognize the SRP promoters described above and used to increase or decrease SRP expression in a plant, thereby modulating the growth and/or stress tolerance of the plant. The present invention also includes identification of the homologs of PpAKT-3 as defined in SEQ ID NO:1, GmAKT-2 as defined in SEQ ID NO:3, and TaAKT-1 as defined in SEQ ID NO:5 in a target plant, as well as the homolog's promoter. The invention also provides a method of increasing expression of a gene of interest within a host cell as compared to a wild type variety of the host cell, wherein the gene of interest is transcribed in response to an SRP, comprising: (a) transforming the host cell with an expression vector comprising an SRP coding nucleic acid, and (b) expressing the SRP within the host cell, thereby increasing the expression of the gene transcribed in response to the SRP, as compared to a wild type variety of the host cell.

In addition to introducing the SRP nucleic acid sequence into transgenic plants, this sequence can also be used to identify an organism as being *P. patens, G. max*, or *T. aestivum*, or a close relative thereof. Also, they may be used to identify the presence of *P. patens, G. max*, or *T. aestivum*, or a relative thereof in a mixed population of microorganisms. The invention provides the nucleic acid sequence of *P. patens, G. max*, and *T. aestivum* genes; by probing the extracted genomic DNA of a culture of a unique or mixed population of microorganisms under stringent conditions with a probe spanning a region of a *P. patens, G. max*, or *T. aestivum* gene that is unique to this organism, one can ascertain whether this organism is present.

Further, the nucleic acid and polypeptide molecules of the invention may serve as markers for specific regions of the genome. This has utility not only in the mapping of the genome, but also in functional studies of *P. patens, G. max*, or *T. aestivum* polypeptides. For example, to identify the region of the genome to which a particular *P. patens* DNA-binding polypeptide binds, the *P. patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *P. patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The SRP nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the SRP nucleic acid molecules of the invention may result in the production of SRPs having functional differences from the wild-type SRPs. These polypeptides may be improved in efficiency or activity, may be present in greater numbers in the cell than is usual, or may be decreased in efficiency or activity.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993, Biotechnology, vol. 3, Chapter III: Product recovery and purification, page 469-714, VCH: Weinheim; Better et al., 1988, Bioseparations: downstream processing for biotechnology, John Wiley and Sons; Kennedy and Cabral, 1992, Recovery processes for biological materials, John Wiley and Sons; Shaeiwitz and Henry, 1988, Biochemical separations, in: Ulmann's Encyclopedia of Industrial Chemistry, vol. B3, Chapter 11, page 1-27, VCH: Weinheim; and Dechow, 1989, Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stresses. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their tolerance to drought, salt, and temperature stresses.

The engineering of one or more SRP genes of the invention may also result in SRPs having altered activities which indirectly impact the stress response and/or stress tolerance of algae, plants, ciliates, or fungi, or other microorganisms like *C. glutamicum*. For example, the normal biochemical processes of metabolism result in the production of a variety of products (e.g., hydrogen peroxide and other reactive oxygen species), which may actively interfere with these same metabolic processes. For example, peroxynitrite is known to nitrate tyrosine side chains, thereby inactivating some enzymes having tyrosine in the active site (Groves, 1999, Curr. Opin. Chem. Biol. 3(2): 226-235). While these products are typically excreted, cells can be genetically altered to transport more products than is typical for a wild-type cell. By optimizing the activity of one or more SRPs of the invention that are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, 1998, The Plant Journal 15: 39-48). The resultant knockout cells can then be evaluated for their ability or capacity to tolerate various stress conditions, their response to various stress conditions, and the effect on the phenotype and/or genotype of the mutation. For other methods of gene inactivation, see U.S. Pat. No. 6,004,804 "Non-Chimeric Mutational Vectors" and Puttaraju et al., 1999, Spliceosome-mediated RNA trans-splicing as a tool for gene therapy, Nature Biotechnology 17: 246-252.

The aforementioned mutagenesis strategies for SRPs resulting in increased growth under normal or stress conditions and/or increased stress resistance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like *C. glutamicum* expressing mutated SRP nucleic acid and polypeptide molecules such that the growth under normal or stress conditions and/or stress tolerance is improved.

The present invention also provides antibodies that specifically bind to an SRP, or a portion thereof, as encoded by a nucleic acid described herein. Antibodies can be made by many well-known methods (See, e.g., Harlow and Lane, "Antibodies; A Laboratory Manual," Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced (See, for example, Kelly et al., 1992, Bio/Technology 10: 163-167; Bebbington et al., 1992, Bio/Technology 10: 169-175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual," Cold Spring Harbor Publications, New York, 1988, for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *P. patens* (Hedw.) B.S.G. from the collection of the genetic studies section of the University of Hamburg were used. They originate from the strain 16/14 collected by H.L.K. Whitehouse in Gransden Wood, Huntingdonshire (England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromols$^{-1}$ m$^{-2}$ (white light; Philips TL 65W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol, and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al. 1989. Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of H$_2$O+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and poly-(A)+ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al. 1994, Mol. Gen. Genet., 244: 352-359). The Poly(A)+ RNA was isolated using Dyna Beads$^R$ (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al., 1989, Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

5'-CAGGAAACAGCTATGACC-3'    SEQ ID NO: 7

5'-CTAAAGGGAACAAAAGCTG-3'   SEQ ID NO: 8

5'-TGTAAAACGACGGCCAGT-3'    SEQ ID NO: 9

Sequences were processed and annotated using the software package EST-MAX commercially provided by BioMax (Munich, Germany). The program incorporates practically all bioinformatics methods important for functional and structural characterization of protein sequences. For reference, see the website at pedant.mips.biochem.mpg.de. The most important algorithms incorporated in EST-MAX are: FASTA (Very sensitive sequence database searches with estimates of statistical significance; Pearson, 1990, Rapid and sensitive sequence comparison with FASTP and FASTA, Methods Enzymol. 183:63-98); BLAST (Very sensitive sequence database searches with estimates of statistical significance; Altschul et al., Basic local alignment search tool, Journal of Molecular Biology 215:403-10); PREDATOR (High-accuracy secondary structure prediction from single and multiple sequences; Frishman and Argos, 1997, 75% accuracy in protein secondary structure prediction. Proteins 27:329-335); CLUSTALW (Multiple sequence alignment; Thompson et al., 1994, CLUSTAL W (improving the sensitivity of progressive multiple sequence alignment through sequence weighting, positions-specific gap penalties and weight matrix choice), Nucleic Acids Research 22:4673-4680); TMAP (Transmembrane region prediction from multiply aligned sequences; Persson and Argos, 1994, Prediction of transmembrane segments in proteins utilizing multiple sequence alignments, J. Mol. Biol. 237:182-192); ALOM2 (Transmembrane region prediction from single sequences; Klein et al., Prediction of protein function from sequence properties: A discriminate analysis of a database. Biochim. Biophys. Acta 787:221-226 (1984). Version 2 by Dr. K. Nakai); PROSEARCH (Detection of PROSITE protein sequence patterns; Kolakowski et al., 1992, ProSearch: fast searching of protein sequences with regular expression patterns related to protein structure and function. Biotechniques 13, 919-921); BLIMPS (Similarity searches against a database of ungapped blocks, Wallace and Henikoff, 1992); PATMAT (a searching and extraction program for sequence, pattern and block queries and databases, CABIOS 8:249-254. Written by Bill Alford).

Example 5

Identification of *Physcomitrella patens* ORFs Corresponding to PpAKT-3

*P. patens* partial cDNAs (ESTs) were identified in the *P. patens* EST sequencing program using the program EST-MAX through BLAST analysis. The full-length nucleotide cDNA sequence of PpAKT-3 is defined as SEQ ID NO:1. The ORF of PpAKT-3 (EST472) encodes the 825 amino acid polypeptide shown in SEQ ID NO:2, including the potassium transporter domain from amino acid position 78 to amino acid position 772 of SEQ ID NO:2. The identity and similarity of the amino acid sequence of PpAKT-3 to known protein sequences are shown in Table 1.

TABLE 1

Degree of Amino Acid Identity and Similarity of PpAKT-3 and Other Homologous Proteins

| Public Database Accession# | Protein Name | Species | Sequence Identity (%) | Sequence Similarity (%) |
|---|---|---|---|---|
| Q8VXB2 | Putative potassium transporter | *Oryza Sativa* | 51.8 | 66.9 |
| Q8VXB1 | Putative potassium transporter | *Oryza sativa* | 50.5 | 67.1 |
| Q653B6 | Putative potassium transporter | *Oryza sativa* | 51.9 | 67.2 |
| G86436 | Barley probable Potassium transport protein | *Arabidopsis thaliana* | 51.0 | 66.5 |
| Q9M7K3 | HAK2 potassium ion transporter | *Hordeum vulgare* | 46.7 | 60.6 |

Example 6

Cloning of the Full-Length *P. patens* cDNA Encoding PpAKT-3

To isolate the clone encoding PpAKT-3 (SEQ ID NO:1) from *P. patens*, cDNA libraries were created with SMART RACE cDNA Amplification kit (Clontech Laboratories) following manufacturer's instructions. Total RNA isolated as described in Example 3 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points as for salt.

5' RACE Protocol

The EST sequences identified from the database search as described in Example 4 were used to design oligos for RACE (See Table 2). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding region and were used to design oligos for full-length cloning of the respective gene (See below full-length amplification).

Full-length Amplification

Full-length clones corresponding to PpAKT-3 (SEQ ID NO:1) obtained by performing polymerase chain reaction (PCR) with gene-specific primers (See Table 2) and the original EST as the template. The conditions for the reaction were standard conditions with PWO DNA polymerase (Roche). PCR was performed according to standard conditions and according to manufacturer's protocols (Sambrook et al., 1989, Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty-five cycles of one minute at 94° C., one minute at 65° C. and 1.5 minutes at 72° C.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al., 1989, Molecular Cloning, A Laboratory Manual. 2nd Edition. Cold Spring Harbor Laboratory Press. Cold Spring Harbor, N.Y.). Transformed cells were selected for on LB agar containing 100 μg/ml carbenicillin, 0.8 mg X-gal (5-bromo-4-chloro-3-indolyl-β-D-galactoside), and 0.8 mg IPTG (isopropylthio-β-D-galactoside) grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989, Molecular Cloning, A Laboratory Manual. 2nd Edition. Cold Spring Harbor Laboratory Press. Cold Spring Harbor, N.Y.).

were processed. After each hybridization, a blot image was captured during a phosphorimage scan to generate a hybridization profile for each oligonucleotide. This raw data image was automatically transferred via LIMS to a computer. Absolute identity was maintained by barcoding for the image cassette, filter, and orientation within the cassette. The filters were then treated using relatively mild conditions to strip the bound probes and returned to the hybridization chambers for another round of hybridization. The hybridization and imaging cycle was repeated until the set of 288 oligomers was completed.

After completion of the hybridizations, a profile was generated for each spot (representing a cDNA insert), as to which of the 288 $^{33}$P radiolabeled 7-mer oligonucleotides bound to that particular spot (cDNA insert), and to what degree. This profile is defined as the signature generated from that clone.

TABLE 2

Scheme and primers used for cloning of the full-length clones

| Gene | Final Product Sites | Isolation Method | Primers Race | Primers RT-PCR |
|---|---|---|---|---|
| PpAKT-3 | XmaI/ EcoRV | 5' Race PCR and RT-PCR for the full-length clone | (SEQ ID NO: 10) CTGAAGCCGGTTTGGAGTG ATCGTC RC523: (SEQ ID NO: 11) GGAGGGTGGTGACGATCAT GACCATCAC RC738: (SEQ ID NO: 12) CCAGCTGTGACGCAGAGGC AGAGAAC RC756: (SEQ ID NO: 13) ACCAGCGGCACCCAGCCTC CTTGAG RC757: (SEQ ID NO: 14) AGGCAAGGAGGAAGTGCTT CCGCCAA | RC856: (SEQ ID NO: 15) ATCCCGGGCGATT GCCTGCTCTGAAT GATCAG RC857: (SEQ ID NO: 16) GCGTTAACGTCGC CCTGTACAAAACT CAGACCCA |

Example 7

Identification of PpAKT-3 Homologs

Tissue Harvest, RNA Isolation, and cDNA Library Construction

Soybean, wheat, and canola plants were grown under a variety of conditions and treatments, and different tissues were harvested at various developmental stages. Plant growth and harvesting were done in a strategic manner such that the probability of harvesting all expressable genes in at least one or more of the resulting libraries is maximized. The mRNA was isolated as described in Example 3 from each of the collected samples, and cDNA libraries were constructed. No amplification steps were used in the library production process in order to minimize redundancy of genes within the sample and to retain expression information. All libraries were 3' generated from mRNA purified on oligo dT columns. Colonies from the transformation of the cDNA library into E. coli were randomly picked and placed into microtiter plates.

Probe Hybridization

Plasmid DNA was isolated from the E. coli colonies and then spotted on membranes. A battery of 288 $^{33}$P radiolabeled 7-mer oligonucleotides were sequentially hybridized to these membranes. To increase throughput, duplicate membranes Each clone's signature was compared with all other signatures generated from the same organism to identify clusters of related signatures. This process "sorts" all of the clones from an organism into clusters before sequencing.

Gene Isolation

The clones were sorted into various clusters based on their having identical or similar hybridization signatures. A cluster should be indicative of the expression of an individual gene or gene family. A by-product of this analysis is an expression profile for the abundance of each gene in a particular library. One-path sequencing from the 5' end was used to predict the function of the particular clones by similarity and motif searches in sequence databases.

The full-length DNA sequence of the *P. patens* PpAKT-3 (SEQ ID NO:1) was blasted against proprietary databases of soybean, wheat, and canola at E value of E-10. (Altschul, Stephen et al., Gapped BLAST and PSI_BLAST: a new generation of protein database search program, Nucleic Acids Res. 25: 3389-3402). All the contig hits were analyzed for the putative full-length sequences, and the longest clones representing the putative full-length contigs were fully sequenced. One sequence from soybean and one sequence from wheat were identified. These are GmAKT-2 and TaAKT-1. The homology of the GmAKT-2 and TaAKT-1 amino acid sequences to the closest known prior art sequence is indicated in Tables 3 and 4

TABLE 3

Degree of Amino Acid Identity and Similarity of GmAKT-2 and a Similar Protein

| Gene Name | Public Database Sequence | Protein Name | Species | Sequence Identity (%) | Sequence Similarity (%) |
|---|---|---|---|---|---|
| GmAKT-2 | POT4_ARATH | Potassium transporter 4 | *Arabidopsis thaliana* | 76% | 84% |

TABLE 4

Degree of Amino Acid Identity and Similarity of TaAKT-1 and a Similar Protein

| Gene Name | Public Database Sequence | Protein Name | Species | Sequence Identity (%) | Sequence Similarity (%) |
|---|---|---|---|---|---|
| TaAKT-1 | NP_914903 | Putative high affinity potassium transporter | *Oryza sativa* | 80% | 84% |

TABLE 5

Degree of Amino Acid Identity of PpAKT-3, GmAKT-2, and TaAKT-1 proteins

|  | PpAKT-3 | GmAKT-2 | TaAKT-1 |
|---|---|---|---|
| PpAKT-3 | 100% | 45.9% | 43.2% |
| GmAKT-2 |  | 100% | 40.4% |
| TaAKT-1 |  |  | 100% |

The ORF of GmAKT-2 (GM59666231) encodes the 821 amino acid polypeptide shown in SEQ ID NO: 4, including the potassium transporter domain from the amino acid position 43 to amino acid 768. The ORF of TaAKT-1 (TA59824966) encodes the 785 amino acid polypeptide shown in SEQ ID NO: 6, including the potassium transporter domain from the amino acid position 82 to amino acid 732.

Example 8

Engineering Stress-Tolerant *Arabidopsis* Plants by Overexpressing an AKT Gene

Cloning of the AKT Genes into a Binary Vector

The fragments containing the *P. patens* AKT genes (e.g., PpAKT-3) were subcloned from the recombinant PCR2.1 TOPO vectors by double digestion with restriction enzymes according to manufacturer's instructions. The subsequent fragment was excised from agarose gel with a QIAquick Gel Extraction Kit (Qiagen) according to manufacturer's instructions and ligated into a binary vector containing a selectable marker gene. The resulting recombinant vector contained the corresponding AKT gene in the sense orientation under the constitutive super promoter.

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*A. thaliana* ecotype C24 plants were grown and transformed according to standard conditions (Bechtold, 1993, Acad. Sci. Paris. 316: 1194-1199; Bent et al., 1994, Science 265: 1856-1860).

Screening of Transformed Plants

T1 plants were screened for resistance to the selection agent conferred by the selectable marker gene, and T1 seeds were collected. T1 seeds were sterilized according to standard protocols (Xiong et al., 1999, Plant Molecular Biology Reporter 17: 159-170). Seeds were plated on ½ Murashige and Skoog media (MS) (Sigma-Aldrich) pH 5.7 with KOH, 0.6% agar and supplemented with 1% sucrose, 0.5 g/L 2-[N-Morpholino]ethansulfonic acid (MES) (Sigma-Aldrich), 50-150 µg/ml selection agent, 500 µg/ml carbenicillan (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromols$^{-1}$ m$^{-2}$ (white light; Philips TL 65W/25 fluorescent tube) and 16 hours light and 8 hours dark day length cycle. Transformed seedlings were selected after 14 days and transferred to ½ MS media pH 5.7 with KOH 0.6% agar plates supplemented with 0.6% agar, 1% sucrose, 0.5 g/L MES (Sigma-Aldrich), and 2 µg/ml benomyl (Sigma-Aldrich) and allowed to recover for five to seven days.

Growth Screening Under Water-Limited Conditions

The PpAKT-3 gene was overexpressed in *A. thaliana* under the control of a constitutive promoter. T2 and/or T3 seeds were screened for resistance to the selection agent conferred by the selectable marker gene on plates, and positive plants were transplanted into soil and grown in a growth chamber for 3 weeks. Soil moisture was maintained throughout this time at approximately 50% of the maximum water-holding capacity of soil.

The total water lost (transpiration) by the plant during this time was measured. After 3 weeks, the entire above-ground plant material was collected, dried at 65° C. for 2 days and weighed. The results are shown in Tables 6 and 7. The ratio of above-ground plant dry weight (DW) to plant water use is Water Use Efficiency (WUE). Tables 6 and 7 present WUE and DW, respectively, for independent transformation events (lines). Least square means, standard errors, and significant value (p) of a line compared to wild-type controls from an Analysis of Variance are presented. The percent improvement from wild-type control plants for WUE (Table 6) and DW (Table 7) for PpAKT-3 (EST 472) overexpressing plants are also presented.

TABLE 6

| Measurement | Genotype | Line | Least Square Mean | Standard Error | % Improvement | p |
|---|---|---|---|---|---|---|
| WUE | Wild-type |  | 1.620 | 0.064 |  |  |
|  | PpAKT-3 | 1 | 2.238 | 0.225 | 38 | 0.0091 |
|  | (EST 472) | 2 | 2.036 | 0.201 | 26 | 0.0506 |
|  |  | 5 | 2.246 | 0.225 | 39 | 0.0083 |

TABLE 6-continued

| Measurement | Genotype | Line | Least Square Mean | Standard Error | % Improvement | p |
|---|---|---|---|---|---|---|
| | | 7 | 2.119 | 0.201 | 31 | 0.0194 |
| | | 8 | 2.096 | 0.201 | 29 | 0.0256 |
| | | 9 | 2.125 | 0.201 | 31 | 0.018 |
| | | 10 | 2.134 | 0.201 | 32 | 0.016 |

TABLE 7

| Measurement | Genotype | Line | Least Square Mean | Standard Error | % Improvement | p |
|---|---|---|---|---|---|---|
| DW | Wild-type | | 0.110 | 0.005 | | |
| | PpAKT-3 | 1 | 0.129 | 0.018 | 17 | 0.3102 |
| | (EST 472) | 2 | 0.146 | 0.016 | 32 | 0.0347 |
| | | 5 | 0.149 | 0.018 | 35 | 0.0399 |
| | | 7 | 0.123 | 0.016 | 12 | 0.4449 |
| | | 8 | 0.160 | 0.016 | 45 | 0.0035 |
| | | 9 | 0.147 | 0.016 | 33 | 0.0318 |
| | | 10 | 0.164 | 0.016 | 48 | 0.0017 |

Drought Tolerance Screening

T1 seedlings were transferred to dry, sterile filter paper in a petri dish and allowed to desiccate for two hours at 80% RH (relative humidity) in a Percieval Growth Cabinet MLR-350H, micromols$^{-1m2}$ (white light; Philips TL 65W/25 fluorescent tube). The RH was then decreased to 60% and the seedlings are desiccated further for eight hours. Seedlings were then removed and placed on ½ MS 0.6% agar plates supplemented with 2 μg/ml benomyl (Sigma-Aldrich) and 0.5 g/L MES (Sigma-Aldrich) and scored after five days.

Example 9

Detection of the AKT Transgene in the Transgenic *Arabidopsis* Lines

Taqman Copy Number Assay

Genomic DNA for TaqMan copy number assays was isolated from leaf samples in 96-well deep-well plates containing a chrome-steel ball, the plates were placed into a minus 80° C. freezer for more than 30 minutes and/or lyophilized overnight. Frozen tissues contained in deep-well plates were ground. Genomic DNA was extracted using the Magnesil® Genomic DNA Extraction kit (Promega, Madison, Wis.) according to manufacturer's instruction.

PCR primers and probes were designed using Primer Express® software (Applied Biosystems, Foster City, Calif.). Primers and probes were designed for both an endogenous control gene as well as a region specific to the transgene present in the construct. Probes were labeled at their 5' end with one reporter fluorophore for the endogenous control and another reporter fluorophore for the transgenes, and both were labeled at the 3' end with a quencher.

Polymerase chain reactions were carried out as described by Ingham et. al. (BioTechniques 31:132-140, 2001) and Ingham (Methods in Molecular Biology 286: 273-289, 2004).

Example 10

Detection of the AKT Transgene mRNA in Transgenic *Arabidopsis* Lines qRT-PCR Assay Total RNA for qRT-PCR assays was isolated from leaf samples in wells of a 1.2 ml 96-well deep-well plates (Corning) containing a chrome-steel ball, the plates were placed into a minus 80° C. freezer for more than 30 minutes and/or lyophilized overnight. The frozen tissue within the deep-well plates was ground. Total RNA was extracted using the Magnesil® Genomic DNA Extraction kit (Promega, Madison, Wis.) according to manufacturer's instruction. The RNA was then DNase treated using the DNA-free kit (Ambion, Austin, Tex.) according to manufacturer's instructions.

PCR primers and probes were designed using Primer Express® software (Applied Biosystems, Foster City, Calif.). Primers and probes were designed for both an endogenous control gene as well as a region specific to the transgene present in the construct. Probes were labeled at their 5' end with one reporter fluorophore for the endogenous control and another reporter fluorophore for the transgenes, and both were labeled at the 3' end with a quencher.

Polymerase chain reactions were carried out in 96-well reaction plates (Applied Biosystems, Foster City, Calif.). The one-step SYBR Green I qRT-PCR mastermix (Eurogentec, San Diego, Calif.) was used according to manufacturer's instructions. Fold difference of expression was calculated utilizing the exported cycle threshold (Ct) values as described by Ingham et. al. (BioTechniques 31:132-140, 2001) and Ingham (Methods in Molecular Biology 286: 273-289, 2004).

Example 11

Engineering Stress-Tolerant Rapeseed/Canola Plants by Overexpressing an AKT Gene Cotyledonary petioles of 4 day-old young seedlings are used as explants for tissue culture and transformed according to patent EP1566443. The commercial cultivar Westar (Agriculture Canada) is the standard variety used for transformation, but other varieties can be used.

*Agrobacterium tumefaciens* GV3101:pMP90RK containing a binary vector is used for canola transformation. The standard binary vector used for transformation is pSUN (patent WO02/00900), but many different binary vector systems have been described for plant transformation (e.g. An, G. in *Agrobacterium* Protocols. Methods in Molecular Biology vol 44, pp 47-62, Gartland KMA and MR Davey eds. Humana Press, Totowa, N.J.). A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (US patents 5767366 and 6225105). Similarly, various promoters can be used to regulate the trait gene to provide constitutive, developmental, tissue or environmental regulation of gene transcription. In this example, the 34S promoter (GenBank Accession numbers M59930 and X16673) is used to provide constitutive expression of the trait gene.

Canola seeds are surface-sterilized in 70% ethanol for 2 min, incubated for 15 min in 55° C. warm tap water and then in 1.5% sodium hypochlorite for 10 min, followed by three rinses with sterilized distilled water. Seeds are then placed on MS medium without hormones, containing Gamborg B5 vitamins, 3% sucrose, and 0.8% Oxoidagar. Seeds are germinated at 24° C. for 4 days in low light (<50 µMol/m2s) at 16 hr light. The cotyledon petiole explants with the cotyledon attached are excised from the in vitro seedlings, and inoculated with *Agrobacterium* by dipping the cut end of the petiole explant into the bacterial suspension. The explants are then cultured for 3 days on MS medium incl. vitamins containing 3.75 mg/l BAP, 3% sucrose, 0.5 g/l MES, pH 5.2, 0.5 mg/l GA3, 0.8% Oxoidagar at 24° C., 16 hr light. After three days of co-cultivation with *Agrobacterium*, the petiole explants are transferred to regeneration medium containing 3.75 mg/l BAP, 0.5 mg/l GA3, 0.5 g/l MES, pH 5.2, 300 mg/l timentin and selection agent until shoot regeneration. As soon as explants start to develop shoots, they are transferred to shoot elongation medium (A6, containing full strength MS medium including vitamins, 2% sucrose, 0.5% Oxoidagar, 100 mg/l myo-inositol, 40 mg/l adenine sulfate, 0.5 g/l MES, pH 5.8, 0.0025 mg/l BAP, 0.1 mg/l IBA, 300 mg/l timentin and selection agent).

Samples from both in vitro and greenhouse material of the primary transgenic plants (TO) are analyzed by qPCR using TaqMan probes to confirm the presence of T-DNA and to determine the number of T-DNA integrations.

Seed is produced from the primary transgenic plants by self-pollination. The second-generation plants are grown in greenhouse conditions and self-pollinated. The plants are analyzed by qPCR using TaqMan probes to confirm the presence of T-DNA and to determine the number of T-DNA integrations. Homozygous transgenic, heterozygous transgenic and azygous (null transgenic) plants are compared for their growth characteristics and yield.

Example 12

Engineering Stress-Tolerant Corn Plants by Overexpressing an AKT Gene

*Agrobacterium* cells harboring the genes and the maize ahas gene on the same plasmid were grown in YP medium supplemented with appropriate antibiotics for 1-3 days. A loop of *Agrobacterium* cells was collected and suspended in 2 ml M-LS-002 medium (LS-inf) and the tube containing Agrobactium cells was kept on a shaker for 1-3 hrs at 1,200 rpm.

Corncobs [genotype J553x(HIIIAxA188)] were harvested at 7-12 days after pollination. The cobs were sterilized in 20% Clorox solution for 15 min followed by thorough rinse with sterile water. Immature embryos with size 0.8-2.0 mm were dissected into the tube containing *Agrobacterium* cells in LS-inf solution.

Agro-infection was carried out by keeping the tube horizontally in the laminar hood at room temperature for 30 min. Mixture of the agro infection was poured on to a plate containing the co-cultivation medium (M-LS-011). After the liquid agro-solution was piped out, the embryos were plated on the co-cultivation medium with schutellum side up and cultured in the dark at 22° C. for 2-4 days.

Embryos were transferred to M-MS-101 medium without selection. Seven to ten days later, embryos were transferred to M-LS-401 medium containing 0.75 µM imazethapyr and grown for 4 weeks to select for transformed callus cells.

Plant regeneration was initiated by transferring resistant calli to M-LS-504 medium supplemented with 0.75 µM imazethapyr and grown under light at 2° C. for two to three weeks. Regenerated shoots were then transferred to rooting box with M-MS-607 medium (0.5 µM imazethapyr).

Plantlets with roots were transferred to potting mixture and grown in a growth chamber for a week, then transplanted to larger pots and maintained in greenhouse till maturity.

Example 13

Greenhouse Stress Tolerance Screening for AKT Transgenic Plants

High Throughput Drought Performance Screen

Segregating transgenic corn seeds for a transformation event were planted in small pots. Each of these plants was uniquely labeled, sampled, and analyzed for transgene copy number. Transgene positive and negative plants were marked and paired with similar sizes for transplanting together to large pots. This provided a uniform and competitive environment for the transgene positive and negative plants. The large pots were watered to a certain percentage of the field water capacity of the soil depending the severity of water-stress desired. The soil water level was maintained by watering every other day. Plant growth and physiology traits such as height, stem diameter, leaf rolling, plant wilting, leaf extension rate, leaf water status, chlorophyll content and photosynthesis rate were measured during the growth period. After a period of growth, the above ground portion of the plants was harvested, and the fresh weight and dry weight of each plant were taken. A comparison of phenotype between the transgene positive and negative plants was then made.

Water Use Efficiency (WUE) Assay

Transgene positive and negative corn seedlings for a transformation event were transplanted into a pot with a given amount of soil and water. The pots were covered with caps that permit the seedlings to grow through but minimize water loss. Each pot was weighed periodically and water added to maintain the initial water content. At the end of the experiment, the fresh and dry weight of each plant were measured, the water consumed by each plant was calculated and WUE of each plant was computed. Plant growth and physiology traits such as WUE, height, stem diameter, leaf rolling, plant wilting, leaf extension rate, leaf water status, chlorophyll content and photosynthesis rate were measured during the experiment. A comparison of phenotype between the transgene positive and negative plants was then made.

Desiccation Assay

Segregating transgenic corn seeds for a transformation event were planted in small pots. These pots were kept in an area in the greenhouse that had uniform environmental conditions, and cultivated optimally. Each of these plants was uniquely labeled, sampled, and analyzed for transgene copy number. The plants were allowed to grow under theses conditions until they reach a predefined growth stage. Water was then withheld. Plant growth and physiology traits such as height, stem diameter, leaf rolling, plant wilting, leaf extension rate, leaf water status, chlorophyll content and photosynthesis rate were measured as stress intensity increases. A comparison of the phenotype between transgene positive and negative plants was then made.

Cycling Drought Assay

Segregating transgenic corn seeds for a transformation event were planted in small pots. These pots were kept in an area in the greenhouse that had uniform environmental conditions, and cultivated optimally. Each of these plants was uniquely labeled, sampled, and analyzed for transgene copy number. The plants were allowed to grow under theses conditions until they reached a predefined growth stage. Plants were then repeatedly watered to saturation at a fixed interval of time. This water/drought cycle was repeated for the duration of the experiment. Plant growth and physiology traits such as height, stem diameter, leaf rolling, leaf extension rate, leaf water status, chlorophyll content and photosynthesis rate were measured during the growth period. At the end of the experiment, the plants were harvested for above-ground fresh and dry weight. A comparison of the phenotype between transgene positive and negative plants was then made.

Example 14

Field Stress Tolerance Screening for AKT Transgenic Plants

Segregating Corn Drought-Tolerance Screening Under Rain-Free Conditions

Managed-drought stress at a single location or multiple locations is used. Crop water availability is controlled by drip tape or overhead irrigation at a location which has less than 10 cm rainfall and minimum temperatures greater than 5° C. expected during an average 5-month season, or a location with expected in-season precipitation intercepted by an automated "rain-out shelter," which retracts to provide open field conditions when not required. Standard agronomic practices in the area are followed for soil preparation, planting, fertilization, and pest control. Each plot is sown with seed segregating for the presence of a single transgenic insertion event. A Taqman transgene copy number assay (as described in Example 9) is used on leaf samples to differentiate the transgenics from null-segregant control plants. Plants that have been genotyped in this manner are also scored for a range of phenotypes related to drought-tolerance, growth, and yield. These phenotypes include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plants are used as the replicate unit per event.

Non-Segregating Corn Drought-Tolerance Screening Under Rain-Free Conditions

Managed-drought stress at a single location or multiple locations is used. Crop water availability is controlled by drip tape or overhead irrigation at a location which has less than 10 cm rainfall and minimum temperatures greater than 5° C. expected during an average 5 month season, or a location with expected in-season precipitation intercepted by an automated "rain-out shelter," which retracts to provide open field conditions when not required. Standard agronomic practices in the area are followed for soil preparation, planting, fertilization, and pest control. Trial layout is designed to pair a plot containing a non-segregating transgenic event with an adjacent plot of null-segregant controls. Progeny (or lines derived from the progeny) of a transgenic plant that does not contain the transgene due to Mendelian segregation. Additional replicated paired plots for a particular event are distributed around the trial. A range of phenotypes related to drought-tolerance, growth and yield are scored in the paired plots and estimated at the plot level. When the measurement technique could only be applied to individual plants, these are selected at random each time from within the plot. These phenotypes include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

Multi-Location Corn Drought-Tolerance and Yield Screening

Five to twenty locations encompassing major corn growing regions are selected. These are widely distributed to provide a range of expected crop water availabilities based on average temperature, humidity, precipitation, and soil type. Crop water availability is not modified beyond standard agronomic practices. Trial layout is designed to pair a plot containing a non-segregating transgenic event with an adjacent plot of null-segregant controls. A range of phenotypes related to drought-tolerance, growth and yield are scored in the paired plots and estimated at the plot level. When the measurement technique could only be applied to individual plants, these are selected at random each time from within the plot. These phenotypes included plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

APPENDIX

```
Nucleotide sequence of PpAKT-3 from Physcomitrella
patens (EST 472) (SEQ ID NO: 1)
ATCCCGGGCGATTGCCTGCTCTGAATGATCAGTGTGGTGAGTGAAGGAAC

TGTGGCTAGTGTGCCCGCCATTGTGCTCGCCGTCTGAGGATCATGTCGAC

CACTACGGTGTCGGAGGACGCCGAAGATGGGAGAGGTGGTCGCAACGGCC

AGCAGGCCAACCAAGGGCGCCTGTGGGACATGGATCAGCGGATCGACCAG

CCGCTGGGTGCCGAAGCCGACCATGTTAGGTCCATGTATCGCGACCAGAC

TATGCCTCCGAGTGTGGTGTTGTGCCTAGCGTTTCAGAGCCTTGGGGTGG

TCTACGGAGACTTGGGCACATCACCGTTGTATGTTTTCAAGAGCACGTTT

GCTAATGGAGGAGTGAGGAACGAGGATGACATCATTGGAGCTCTATCCCT

CATTATCTACACCCTCACCATTATCCCCTTGATTAAATACGTCTTCATCG

TGCTCAGAGCAAATGACAATGGCGAAGGGGGTTCTTTCGCTCTCTATTCA

TTGCTGTGTCGTTACTGTAATATAAGCGCCCTGCCAAATCAACACCCTTC
```

```
CGATGCGGAGCTTACCACGTATGTCGTAGACAACGCCCGCCGCAAAACCT
GGATTCAGAGGAAGCTGGAAAGTAGTGTGCTTGCGCAGCAAGTGTTGTTG
GTTATTGTGCTCTTCGGGACTTGCATGGTTATCGGCGACGGCATATTAAC
CCCGTCTATCTCAGTCTTATCGGCAGTTGTTGGAATTAAAGCTGCTTCTT
CCTCCTTGGATACTAATTTGGTGACAGGCATTTCGTGCGTCATCTTAGTC
ATCCTCTTTAGCGTACAGCGCTTCGGCACAGCGAAAATCTCAGTCTTGTT
CGCACCGATTTTCTTGGTTTGGTTCCTATCTCTTGCCTGTATCGGCTGCT
ACAACATAATCAAATGGGAGAAATCAATCTTCTTAGCCTTCAATCCCCTT
CAAATCGTACACTTCTTCAGACGGAATGGAAGACAGGGGTGGGAGCATCT
CGGAGGCATCGTGCTGTGTATGACAGGGACTGAAGCGTTGTTTGCCGACT
TGGGCCATTTCAGTTGTCGGTCTATTCAGATTGTCTTCACTTCTCTAGTG
TACCCGTGCTTATTTCTGACTTACCTCGGGCAAGCTGCTTACCTCGTGGA
ACATATGGAAGACGTTAACGATCCCTTTTATTCCTCACTGCCGAGTAGTA
TTTACTGGCCAATCTTCGTGCTGGCAACAATATCAGCCATGATAGCGAGC
CGAGCCATGATCTCCGCCACGTTTTCTATCGTGAAGCAGGCGACAGCTCT
GGGATGCTTTCCTCGAGTGAAGGTTGTGCACACATCAAATAATGTTGCAG
GACAGGTGTATATCCCCGAAATCAACTGGATTCTTATGGTTCTCTGCCTC
TGCGTCACAGCTGGTTTCCGAGACACGGACCAAATCGGAAATGCTTACGG
TATCGCCGTGGTGATGGTCATGATCGTCACCACCCTCCTGATGACCCTAG
TGATAATCATCATTTGGCGGAAGCACTTCCTCCTTGCCTTGCTATTCCTT
GTCGTGTTCGCATCAATCGAGGGAATTTATGTCAGTGCGGTCCTATTCAA
GACAACTCAAGGAGGCTGGGTGCCGCTGGTCATTTCGGTGGTCTTCGGCA
CAGTCATGGGCACATGGCATTACGGAACCTTGAAACGCTACCAGTATGAG
ATGCAGCACAAGGTTTCAGTGGGATGGTTGCTTGGGCTTGGACCTAGCCT
CGGCCTCGTTCGTGTCCCCGGAATCGGTCTCATGTACACAGATCTCGCTC
ATGGAGTGCCGCCGCTATTCTCGCATTTCATCACCAATCTCCCCGCCATC
CATTCCACCGTAGTCTTCGTCTGCGTTAAATACCTGCCAGTGAACACGGT
ACCACAAGATGAGAGATTTCTAATCCGTCGCATCGGTTCAAGAGCTTATT
CCATGTACCGTTGTGCAGCACGTTACGGCTACATAGACCTCCACAAGAAA
GATGACAACTTCGAGCAACTGCTAATTCAAAGCTTAATCAGTTTCGTCGA
GATTGAGTCTATGAGAGAGAGCTCAGGCCGGGAGTCCATGGCTGCAAGCT
GGACCCCAGATCAACAGCCGATGGAGGAGGCCACGGTGCCAACTACGTCG
ACGATCACTCCAAACCGGCTTCAGTTGCAAAGAATGCTGAGATTACACAG
TCTGATGGGCGGAGGCAACAGCGTCGGCGACGGTTATTCCACTCAGTACT
CCCAGACCGCCTCGAACTCGGTCGAGATGTCTGCTAACCAGGAATGCAGT
ATTCCAAACCTGAGCGTCAACGGCAGCAACAGCAGCAGCCCGCATCC
GCAAGACGAAGTTGCCTTCCTGAATGCATGCAAAGATGCTGGCGTGGTGT
ACATACTCGGTAACAACATCGTGAAAGCGAGAAAGGATGCAGGATTTTTC
AAGAAGCTGGTGATCAACTACATGTATACCTTTCTGCGAAGGATAAGCCG
AGACAGCAGCGTGGTGCTCAACATCCCGCACGAGTGCCTACTTCATGTCG
GCATGGTGTACTATGTTTGATTCTTTTGGGTCTGAGTTTTGTACAGGGCG
ACGTTAACGC
```

Deduced amino acid sequence of PpAKT-3 from
Physcomitrella patens (SEQ ID NO: 2)
```
MSTTTVSEDAEDGRGGRNGQQANQGRLWDMDQRIDQPLGAEADHVRSMYR
DQTMPPSVVLCLAFQSLGVVYGDLGTSPLYVFKSTFANGGVRNEDDIIGA
LSLIIYTLTIIPLIKYVFIVLRANDNGEGGSFALYSLLCRYCNISALPNQ
HPSDAELTTYVVDNARRKTWIQRKLESSVLAQQVLLVIVLFGTCMVIGDG
ILTPSISVLSAVVGIKAASSSLDTNLVTGISCVILVILFSVQRFGTAKIS
VLFAPIFLVWFLSLACIGCYNIIKWEKSIFLAFNPLQIVHFFRRNGRQGW
EHLGGIVLCMTGTEALFADLGHFSCRSIQIVFTSLVYPCLFLTYLGQAAY
LVEHMEDVNDPFYSSLPSSIYWPIFVLATISAMIASRAMISATFSIVKQA
TALGCFPRVKVVHTSNNVAGQVYIPEINWILMVLCLCVTAGFRDTDQIGN
AYGIAVVMVMIVTTLLMTLVIIIWRKHFLLALLFLVVFASIEGIYVSAV
LFKTTQGGWVPLVISVVFGTVMGTWHYGTLKRYQYEMQHKVSVGWLLGLG
PSLGLVRVPGIGLMYTDLAHGVPPLFSHFITNLPAIHSTVVFVCVKYLPV
NTVPQDERFLIRRIGSRAYSMYRCAARYGYIDLHKKDDNFEQLLIQSLIS
FVEIESMRESSGRESMAASWTPDQQPMEEATVPTTSTITPNRLQLQRMLR
LHSLMGGGNSVGDGYSTQYSQTASNSVEMSANQECSIPNLSVNGSNSSSS
PHPQDEVAFLNACKDAGVVYILGNNIVKARKDAGFFKKLVINYMYTFLRR
ISRDSSVVLNIPHECLLHVGMVYYV*
```

Nucleotide sequence of GmAKT-2 (GM59666231) from
Glycine max (SEQ ID NO: 3):
```
ATTAAAGGAATCATCCAAAGGGAACTCAAAATGAAATGAAATGGAAATGT
AAGAAGTAGTACTGAAAACTGAACTCAACTAACTCGTGACTCGTCAGAGA
GAAGAAAAGAATATCGTTCGTTCGCTCTTACCTTCTTCACCTTCCTTCCT
CTCTCTCTCTAGAGAATGGAACCGGAATCCGGAACTTCGACTTCTCGGAA
TCCTTCTCAGTTGTCTTGGGTGAATCTGTCTAGGAATTTATTATTAGCGT
ATCAAAGCTTTGGTGTGGTGTATGGAGATCTGAGCACTTCTCCTCTCTAT
GTCTTCACAAGCACCTTCAAGGGGAAGTTGCAGAATCACCATGACGAGGA
AACTATATTCGGCACGTTTTCGTTGATTTTTTGGACCCTTACTTTGATTC
CGTTGCTTAAGTATGTATTCATCCTATTGAGTGCTGATGACAACGGGGAA
GGTGGAACATTCGCTCTTTATTCGCTGCTCTGTAGGCATGCCAAGTTTAA
TTTGCTCCCCAATCAACAAGCAGCTGATGAGGAGTTATCATCCTATAAAT
ATGGTCCCTCTTCACAGGCTATAGCCTCTTCTCCTCTAAAGAGGTTTCTG
GAGAAACATAAAAGGTTAAGAACAGCCCTGCTTGTTGTGGTATTGTTTGG
TGCTTGCATGGTCATTGGTGATGGTGTGCTTACTCCAGCAATTTCGGTTC
TAGCATCAGTCTCAGGACTAAAAGTTACAGAAAAAAAATTAACAGATGGT
GAGCCAAATCTCATTTATTCCTTTTTTTTGTTCTCATCATTGCTTTTGT
TATGCTAAGGGCAAATTGGTTGCAGGTGAACTTGAGAAATTTCATGTTGT
TTGCAGGTGAACTTGTCCTGCTTGCCTGTGTCATATTGGTTGGACTGTTT
GCTCTCCAACATTGTGGCACACACAAAGTTGCAGTTATGTTTGCACCAAT
TGTAATAATCTGGCTTGTATCAATATTTTCTATTGGGGTGTATAATACAA
```

-continued

```
TTCATTGGAATCCAAAAATAGTCCGTGCTATATCGCCATATTATATCATC
AAGTTTTTTAGCAGGACTGGTAAAGAAGGTTGGGTTTCTCTTGGAGGGAT
ACTTCTTTGTATCACTGGAACTGAAGCTATGTTTGCGGATCTTGGTCATT
TCACTGCTTCGTCAATAAGGCTTGCATTTGCGTTTGTTATATACCCGTGT
TTAGTGGTACAGTATATGGGTCAAGCTGCTTTCTTGTCTAAAAATCTCGA
CTCTGTTGATAACGGTTTTTATGACTCAATACCTGACCCTGTGTTTTGGC
CTGTTTTCATAATCGCCACCCTTGCTGCAATTGTTGGGAGTCAAGCTGTT
ATAACTGCAACTTTCTCCATCATCAAGCAGTGTCATGCGCTTGGTTGCTT
TCCGCGAGTCAAAGTTGTACACACCTCAAAACATATATATGGACAGATCT
ATATCCCAGAAATCAATTGGATACTTATGATCCTAACTCTTGCAATAACC
ATTGGATTTCAGGACACGACCATAATTGGAAATGCTTATGGGTTGGCTTG
TATGACAGTTATGTTCATAACTACATTTCTGATGACACTAGTCGCAATCT
TTGTCTGGCAGAAAAGTGTCTTGATTGCTGTTGTATTTCTTTTATTCCTT
TGGGTGATAGAGGGCGTATATCTATCAGCAGCTTTCATCAAAGTGCCTCA
GGGAGGATGGGTACCTCTAGTCTTATCATTCATCTTCATGATTGTTATGT
ACGTGTGGCATTATGGAACTCGTAGGAAGTACAGCTATGATCTGCACAAC
AAAGTTTCATTGAAATGGTTACTGGGCTTGGGCCCAAGCCTTGGCATTGT
TCGTGTACCTGGGATTGGTCTCATCTACACTGAACTGGCAACAGGCATAC
CTGCAATATTTTCCCATTTTGTAACAAATCTTCCTGCATTTCACCAGGTG
TTGGTTTTTGTTTGTGTAAAATCAGTTCCTGTTCCATATGTTTCACCGGA
AGAACGTTTCCTTATTGGGCGAGTTTGCCCCAGACCATATCGAATGTATA
GGTGCATTGTCAGATATGGTTACAAGGACATTCAAAGGGATGATGGAGAT
TTTGAGAATCATCTTATACAGAGTATAGCAGAATTTATCCAAATGGAAGC
AGTGCAACCTCAGTTCTCAAGTTCCGAAGCTTCTTCTTCACTTGATGGGA
GGATGGCCGTTATAAGTTCTAGAAACTATGATTATGCTTCAAGTTTAATA
GTTTCTGAGCAGGAGGATATAGGCGTTGACATATCCATCCCTAGCAGCAG
ATCTGCAACCCTGCAAAGTTTGCAATCGGTTTACGACGATGAAACTCCGC
AAGTTAGAAGACGACGAGTAAGATTTCAGCTACCAGAAAACACTGGTATG
GATCCCGATGTTAGGGAAGAGCTTTTGGATTTAATTCAAGCCAAGGAAGC
TGGGGTTGCATATATAATGGGGCACTCATATGTGAAGGCAAGGAAATCAT
CCTCATTCTTGAAAAAGCTCGTGATTGATATTGGTTACTCATTTCTGCGC
AAGAATTGCAGGGGTCCAGCTGTAGCTCTTAACATTCCTCACATTAGTCT
TATTGAAGTTGGGATGATATATTATGTGTAGTTATTGGTGAAATTTACAA
CTTGATCCTAGTTGCATAGGTAATTAATTGTAGCTCACGGGAAAATGAGT
GTCTTTTGGGGCTACGTGTTTATCTTTGCTTTCGCATCTCTCTCCCAATG
TAATTACATAGTTGCAACAATAAGGTTTTAGAATTATATTTAGGAATCAG
AATATTTTCCTCAAAAAAAAAAAAAAAAAGCGAGAGAGAGACCGACACG
CA
```

Deduced amino acid sequence of GmAKT-2 from *Glycine max* (SEQ ID NO: 4):
MEPESGTSTSRNPSQLSWVNLSRNLLLAYQSFGVVYGDLSTSPLYVFTST
FKGKLQNHHDEETIFGTFSLIFWTLTLIPLLKYVFILLSADDNGEGGTFA
LYSLLCRHAKFNLLPNQQAADEELSSYKYGPSSQAIASSPLKRFLEKHKR
LRTALLVVVLFGACMVIGDGVLTPAISVLASVSGLKVTEKKLTDGEPNLI
YSFFFVLIIAFVMLRANWLQVNLRNFMLFAGELVLLACVILVGLFALQHC
GTHKVAVMFAPIVIIWLVSIFSIGVYNTIHWNPKIVRAISPYYIIKFFSR
TGKEGWVSLGGILLCITGTEAMFADLGHFTASSIRLAFAFVIYPCLVVQY
MGQAAFLSKNLDSVDNGFYDSIPDPVFWPVFIIATLAAIVGSQAVITATF
SIIKQCHALGCFPRVKVVHTSKHIYGQIYIPEINWILMILTLAITIGFQD
TTIIGNAYGLACMTVMFITTFLMTLVAIFVWQKSVLIAVVFLLFLWVIEG
VYLSAAFIKVPQGGWVPLVLSFIFMIVMYVWHYGTRRKYSYDLHNKVSLK
WLLGLGPSLGIVRVPGIGLIYTELATGIPAIFSHFVTNLPAFHQVLVFVC
VKSVPVPYVSPEERFLIGRVCPRPYRMYRCIVRYGYKDIQRDDGDFENHL
IQSIAEFIQMEAVQPQFSSSEASSSLDGRMAVISSRNYDYASSLIVSEQE
DIGVDISIPSSRSATLQSLQSVYDDETPQVRRRRVRFQLPENTGMDPDVR
EELLDLIQAKEAGVAYIMGHSYVKARKSSSFLKKLVIDIGYSFLRKNCRG
PAVALNIPHISLIEVGMIYYV Nucleotide sequence of TaAKT-1 (TA59824966) from *Triticum aestivum* (SEQ ID NO: 5):
```
GTGAGAGAGAGATCATCATCGTACCTGACGATGGCTGAGCCTCTGAAGG
CAAACGGCAATGGAGCTGCCGAAGGGGGTGCTGCGGGCTCTGCGTTTGCA
TCGGTGAAGGTGCCGCCGTCGCCGCCAAGGAGGCTGCAGAGGTTCGACTC
CCTGCATATGGAGGCCGGGAAGATTCCTGGTGGCCACAGCTATGCAGCCA
AGGTTGGCTGGGCGACGACACTGCACTTGGCCTTCCAGAGCCTAGGTGTG
GTTTATGGGGACATGGAACTTCACCCCTCTATGTGTTCTCCAGCACCTT
TACTGGTGGGATCAAGGACACAGATGACCTCCTTGGTGTCATGTCCTTGA
TAATCTATACTGTACTTCTCCTTCCATTGATGAAATATTGTTTCATTGTC
TTGAGAGCTAATGACAACGGCGATGGCGGAACATTTGCACTTTATTCCTT
GATATCTCGGTATGCTAGGATTAGCTTGATACCAAACCAGCAGGCTGAAG
ATGCAACAGTCTCTCACTACAAGTTAGAGTCCCCTACGAATCGTGTCAAG
CGGGCTCATTGGATTAAGGAAAAGATGGAAAACAGCCCGAAATTTAAGGT
CATACTTTTCCTAGTGACAATTCTAGCAACATCAATGGTTATTGGTGACG
GTGTGCTAACTCCATGTATTTCAGTGCTTAGTGCAGTTACGGGAATCAAG
CAATCAGCAAAGTCGTTAACTCAAGGACAAATTGCTGGCATCGCAATCGG
CATTCTGATCGCCCTCTTTCTTGTCCAGCGCTTTGGCACAGACAAAGTTG
GTTACACATTTGGCCCAGTAATCTTTATATGGTTCATCTTAATTGCCGGC
ATTGGAATTTATAATTTGATCAAACATGATACTGGAATTCTGAAAGCATT
CAACCCACAATACATAGTGGAATATTTCCAAAGAAATGGGAAGGACGGCT
GGATTTCGCTTGGAGGTGTTATCTTATGCATTACAGGAACCGAAGCAATG
TTTGCTGACCTTGGTCACTTCAATGTGAGAGCAATTCAGATTGGCCTTTC
TGCAGTTCTGCTCCCATCAGTATTGCTTGCTTACATGGGACAGGCTGCAT
```

ATCTTCGCATCCACCCTGAAGATGTTGCAGATACATTCTACAAATCAATC

CCAGGTCCATTATATTGGCCAACATTTGTGGTGGCCGTGGCTGCTGCTAT

AATTGCAAGCCAAGCTATGATTTCTGGTGCCTTTGCAATCATTGCTCAGT

CCCAAGTTCTTGGTTGCTTTCCACGGGTTCGTGTCACTCACACCTCAAAA

AAGTATCATGGGCAGGTCTACATCCCTGAGATCAACTATGCATTAATGAT

CTTATGTGTAGCTGTGACAGCTATTTTCCAAACTACAGACAAGATTGGCA

ATGCATATGGTATCGCTGTCGTCTTTGTGATGTTCATAACAACACTTCTA

GTCACACTGGTAATGGCCATGATATGGAAGACAAGTCTGCTGTGGATTGC

ACTCTTTCCAATAATATTTGGCGGCGCAGAGCTCGTGTACTTATCCTCAG

CATTCTACAAATTTGTAGAAGGTGGCTACTTGCCACTAGGTTTTGCAGCA

ATTTTGATGCTTATAATGGGCACATGGCACTATGTTCATGTTCATCGGTA

CAAATACGAGCTCAAGAACAAAGTGTCAAACAACTATGTGGCAGATTTGG

CAACAAGGAGAAATCTTGCTAGGTTGCCAGGAATAGGCGTTCTGTACTCT

GAGCTTGTGCAAGGAATCCCACCCATACTGCCCCATTTGGTAGAAAAAGT

ACCTTCCATCCATTCAGTTCTTGTGATTACCTCAATAAAGTACTTACCAA

TCAGCAATATAGAAACAAATGAGCGGTTCCTCTTCCGATACGTGGAGCCA

AGAGAATACAGGGTATTCCGATGTGTGGTGCGCTATGGTTACAACAATAA

AGTAGAAGATCCAAGAGAGTTCGAGAACTTGCTTATTGGGAACTTGAAGC

AATTCATCCATCAAGAATCACTCTACAGCGAAAGTAGTCATTCCCTTGAA

GGAGAAGATAATGCATTCGAAGAATCAGGAGATGCAATGGAGCCTTCTAT

TGAAGTTCAAGATGCAAGGTTGCCGAAAAGGTTTTTAGATGGAATCACTG

CTAGCCCAGTGAACGGGTTAATGGATGAGATAGAGTTTATTCAGAGAGGG

ATGGATGATGGTGTTGTCCATCTGCTGGGAGAAACTAATGTGGTGGCGGA

GCAAAATGCCGGTTTGGTGAAGAAAATAATAGTTGACTACGCCTACAATT

TCATGAGGAAGAACTTCAGGCAACCAGAGAAGATCACATGTGTCCCTCAT

AACAGGCTGCTGCGGGTGGGAATGACATACGAGATCTAGAGAGATGCTCA

GTGGATTGATCAAATTGACAATAGCTTCAGTTTTCTCAGTACCAAGTGCA

GAAAGGATATGCAGAGGAACAGCCTCCTTGACTGAACAGCAGAGGATGGA

GAGATTTTATGCGTACAAGTGGTGAAACTACAGTACATGCAATATGTATT

TACCATATAATATTTTTTTGTTAGGGAAATTCTACTGTATAAGTGTTTG

TTAGCAGTAAGTATGCATAGCTGTCAAACCCCTAGTTTGGCCAACTCTTT

GCCTTATTGTGGAAAACTCAAAATCTTAGTATGTGCAGTTGTACACAAAG

ATTGTAACCTACCGGCAAAAGTTAAACAAATAATAAAGTATGACTTGTGT

GCCAAAAAAAAAAAAAAAAAGAGAGAGAGAGACCGACACGCA

Deduced amino acid sequence of TaAKT-1 from *Triticum aestivum* (SEQ ID NO: 6):
MAEPLKANGNGAAEGGAAGSAFASVKVPPSPPRRLQRFDSLHMEAGKIPG

GHSYAAKVGWATTLHLAFQSLGVVYGDMGTSPLYVFSSTFTGGIKDTDDL

LGVMSLIIYTVLLLPLMKYCFIVLRANDNGDGGTFALYSLISRYARISLI

PNQQAEDATVSHYKLESPTNRVKRAHWIKEKMENSPKFKVILFLVTILAT

SMVIGDGVLTPCISVLSAVTGIKQSAKSLTQGQIAGIAIGILIALELVQR

EGTDKVGYTFGPVIFIWFILIAGIGIYNLIKHDTGILKAFNPQYIVEYFQ

RNGKDGWISLGGVILCITGTEAMFADLGHFNVRAIQIGLSAVLLPSVLLA

YMGQAAYLRIHPEDVADTFYKSIPGPLYWPTFVVAVAAAIIASQAMISGA

FAIIAQSQVLGCFPRVRVTHTSKKYHGQVYIPEINYALMILCVAVTAIFQ

TTDKIGNAYGIAVVFVMFITTLLVTLVMAMIWKTSLLWIALFPIIFGGAE

LVYLSSAFYKFVEGGYLPLGFAAILMLIMGTWHYVHVHRYKYELKNKVSN

NYVADLATRRNLARLPGIGVLYSELVQGIPPILPHLVEKVPSIHSVLVIT

SIKYLPISNIETNERFLFRYVEPREYRVFRCVVRYGYNNKVEDPREFENL

LIGNLKQFIHQESLYSESSHSLEGEDNAFEESGDAMEPSIEVQDARLPKR

FLDGITASPVNGLMDEIEFIQRGMDDGVVHLLGETNVVAEQNAGLVKKII

VDYAYNFMRKNFRQPEKITCVPHNRLLRVGMTYEI

We claim:

1. An isolated polynucleotide selected from the group consisting of:
   (i) a polynucleotide comprising SEQ ID NO:1; and
   (ii) a cDNA encoding a polypeptide comprising SEQ ID NO:2.

2. The isolated polynucleotide of claim 1 comprising SEQ ID NO:1.

3. The isolated cDNA of claim 1 encoding a polypeptide comprising SEQ ID NO:2.

4. The isolated polynucleotide of claim 1, wherein the polynucleotide encodes a polypeptide that functions to increase a plant's growth or stress tolerance under normal or stress conditions as compared to a wild type variety of the plant.

5. A vector comprising an isolated polynucleotide selected from the group consisting of:
   (i) a polynucleotide comprising SEQ ID NO:1; and
   (ii) a polynucleotide encoding a polypeptide comprising SEQ ID NO:2,
   wherein said polynucleotide is operably linked to a heterologous nucleotide sequence.

6. A transgenic plant cell comprising an isolated polynucleotide selected from the group consisting of:
   (i) a polynucleotide comprising SEQ ID NO:1; and
   (ii) a polynucleotide encoding a polypeptide comprising SEQ ID NO:2.

7. A transgenic plant transformed with an isolated polynucleotide selected from the group consisting of:
   (i) a polynucleotide comprising SEQ ID NO:1; and
   (ii) a polynucleotide encoding a polypeptide comprising SEQ ID NO:2.

8. The transgenic plant of claim 7, wherein the plant has increased growth or increased stress tolerance under normal or stress conditions as compared to a wild type variety of the plant.

9. The transgenic plant of claim 7, wherein the plant is a monocot.

10. The transgenic plant of claim 7, wherein the plant is a dicot.

11. The transgenic plant of claim 7, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and a forage crop plant.

12. A transgenic plant seed that is true breeding for an isolated polynucleotide selected from the group consisting of:
    (i) a polynucleotide comprising SEQ ID NO:1; and
    (ii) a polynucleotide encoding a polypeptide comprising SEQ ID NO:2.

13. The transgenic plant seed of claim 12, wherein the seed is true breeding for a transgene comprising SEQ ID NO:1.

14. A method of producing a transgenic plant containing an isolated polynucleotide, wherein the plant has increased growth or increased stress tolerance or increased water use efficiency under normal or stress conditions as compared to a wild type variety of the plant, comprising (a) transforming a plant cell with an expression vector comprising the polynucleotide, and (b) generating from the plant cell the transgenic plant, wherein the polynucleotide is selected from the group consisting of:
    (i) a polynucleotide comprising SEQ ID NO:1; and
    (ii) a polynucleotide encoding a polypeptide comprising SEQ ID NO:2.

15. The method of claim 14, wherein the plant is a monocot.

16. The method of claim 14, wherein the plant is a dicot.

17. The transgenic plant of claim 7, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and a forage crop plant.

18. The method of claim 14, wherein the polynucleotide comprises SEQ ID NO:1.

19. The method of claim 14, wherein the polynucleotide encodes a polypeptide comprising SEQ ID NO:2.

20. The method of claim 14, wherein the expression vector comprises a promoter that directs expression of the polynucleotide.

21. The method of claim 20, wherein the promoter is tissue specific.

22. The method of claim 20, wherein the promoter is developmentally regulated.

* * * * *

SEQUENCE LISTING

```
<160> NUMBER OF SEQ ID NOS: 16

<210> SEQ ID NO 1
<211> LENGTH: 2610
<212> TYPE: DNA
<213> ORGANISM: Physcomitrella patens
<220> FEATURE:
<221> NAME/KEY: CDS
<222> LOCATION: (93)..(2567)
<223> OTHER INFORMATION: PpAKT-3

<400> SEQUENCE: 1
atcccgggcg attgcctgct ctgaatgatc agtgtggtga gtgaaggaac tgtggctagt      60
gtgcccgcca ttgtgctcgc cgtctgagga tc atg tcg acc act acg gtg tcg     113
                                   Met Ser Thr Thr Thr Val Ser
                                   1               5 gag gac gcc gaa gat ggg aga ggt ggt cgc aac ggc cag cag gcc aac      161
Glu Asp Ala Glu Asp Gly Arg Gly Gly Arg Asn Gly Gln Gln Ala Asn
            10                  15                  20
```

| | | |
|---|---|---|
| caa ggg cgc ctg tgg gac atg gat cag cgg atc gac cag ccg ctg ggt<br>Gln Gly Arg Leu Trp Asp Met Asp Gln Arg Ile Asp Gln Pro Leu Gly<br>25                           30                         35 | | 209 |
| gcc gaa gcc gac cat gtt agg tcc atg tat cgc gac cag act atg cct<br>Ala Glu Ala Asp His Val Arg Ser Met Tyr Arg Asp Gln Thr Met Pro<br>40                         45                     50                    55 | | 257 |
| ccg agt gtg gtg ttg tgc cta gcg ttt cag agc ctt ggg gtg gtc tac<br>Pro Ser Val Val Leu Cys Leu Ala Phe Gln Ser Leu Gly Val Val Tyr<br>                   60                     65                     70 | | 305 |
| gga gac ttg ggc aca tca ccg ttg tat gtt ttc aag agc acg ttt gct<br>Gly Asp Leu Gly Thr Ser Pro Leu Tyr Val Phe Lys Ser Thr Phe Ala<br>               75                     80                     85 | | 353 |
| aat gga gga gtg agg aac gag gat gac atc att gga gct cta tcc ctc<br>Asn Gly Gly Val Arg Asn Glu Asp Asp Ile Ile Gly Ala Leu Ser Leu<br>      90                     95                         100 | | 401 |
| att atc tac acc ctc acc att atc ccc ttg att aaa tac gtc ttc atc<br>Ile Ile Tyr Thr Leu Thr Ile Ile Pro Leu Ile Lys Tyr Val Phe Ile<br>105                     110                    115 | | 449 |
| gtg ctc aga gca aat gac aat ggc gaa ggg ggt tct ttc gct ctc tat<br>Val Leu Arg Ala Asn Asp Asn Gly Glu Gly Gly Ser Phe Ala Leu Tyr<br>120                     125                    130                    135 | | 497 |
| tca ttg ctg tgt cgt tac tgt aat ata agc gcc ctg cca aat caa cac<br>Ser Leu Leu Cys Arg Tyr Cys Asn Ile Ser Ala Leu Pro Asn Gln His<br>                140                    145                    150 | | 545 |
| cct tcc gat gcg gag ctt acc acg tat gtc gta gac aac gcc cgc cgc<br>Pro Ser Asp Ala Glu Leu Thr Thr Tyr Val Val Asp Asn Ala Arg Arg<br>                  155                    160                    165 | | 593 |
| aaa acc tgg att cag agg aag ctg gaa agt agt gtg ctt gcg cag caa<br>Lys Thr Trp Ile Gln Arg Lys Leu Glu Ser Ser Val Leu Ala Gln Gln<br>          170                    175                    180 | | 641 |
| gtg ttg ttg gtt att gtg ctc ttc ggg act tgc atg gtt atc ggc gac<br>Val Leu Leu Val Ile Val Leu Phe Gly Thr Cys Met Val Ile Gly Asp<br>185                     190                    195 | | 689 |
| ggc ata tta acc ccg tct atc tca gtc tta tcg gca gtt gtt gga att<br>Gly Ile Leu Thr Pro Ser Ile Ser Val Leu Ser Ala Val Val Gly Ile<br>200                     205                    210                    215 | | 737 |
| aaa gct gct tct tcc tcc ttg gat act aat ttg gtg aca ggc att tcg<br>Lys Ala Ala Ser Ser Ser Leu Asp Thr Asn Leu Val Thr Gly Ile Ser<br>                  220                    225                    230 | | 785 |
| tgc gtc atc tta gtc atc ctc ttt agc gta cag cgc ttc ggc aca gcg<br>Cys Val Ile Leu Val Ile Leu Phe Ser Val Gln Arg Phe Gly Thr Ala<br>                  235                    240                    245 | | 833 |
| aaa atc tca gtc ttg ttc gca ccg att ttc ttg gtt tgg ttc cta tct<br>Lys Ile Ser Val Leu Phe Ala Pro Ile Phe Leu Val Trp Phe Leu Ser<br>          250                    255                    260 | | 881 |
| ctt gcc tgt atc ggc tgc tac aac ata atc aaa tgg gag aaa tca atc<br>Leu Ala Cys Ile Gly Cys Tyr Asn Ile Ile Lys Trp Glu Lys Ser Ile<br>265                     270                    275 | | 929 |
| ttc tta gcc ttc aat ccc ctt caa atc gta cac ttc ttc aga cgg aat<br>Phe Leu Ala Phe Asn Pro Leu Gln Ile Val His Phe Phe Arg Arg Asn<br>280                     285                    290                    295 | | 977 |
| gga aga cag ggg tgg gag cat ctc gga ggc atc gtg ctg tgt atg aca<br>Gly Arg Gln Gly Trp Glu His Leu Gly Gly Ile Val Leu Cys Met Thr<br>                     300                    305                    310 | | 1025 |
| ggg act gaa gcg ttg ttt gcc gac ttg ggc cat ttc agt tgt cgg tct<br>Gly Thr Glu Ala Leu Phe Ala Asp Leu Gly His Phe Ser Cys Arg Ser<br>                  315                    320                    325 | | 1073 |
| att cag att gtc ttc act tct cta gtg tac ccg tgc tta ttt ctg act<br>Ile Gln Ile Val Phe Thr Ser Leu Val Tyr Pro Cys Leu Phe Leu Thr<br>          330                    335                    340 | | 1121 |

```
tac ctc ggg caa gct gct tac ctc gtg gaa cat atg gaa gac gtt aac    1169
Tyr Leu Gly Gln Ala Ala Tyr Leu Val Glu His Met Glu Asp Val Asn
    345             350                 355 gat ccc ttt tat tcc tca ctg ccg agt agt att tac tgg cca atc ttc    1217
Asp Pro Phe Tyr Ser Ser Leu Pro Ser Ser Ile Tyr Trp Pro Ile Phe
360             365                 370                 375 gtg ctg gca aca ata tca gcc atg ata gcg agc cga gcc atg atc tcc    1265
Val Leu Ala Thr Ile Ser Ala Met Ile Ala Ser Arg Ala Met Ile Ser
                380                 385                 390 gcc acg ttt tct atc gtg aag cag gcg aca gct ctg gga tgc ttt cct    1313
Ala Thr Phe Ser Ile Val Lys Gln Ala Thr Ala Leu Gly Cys Phe Pro
            395                 400                 405 cga gtg aag gtt gtg cac aca tca aat aat gtt gca gga cag gtg tat    1361
Arg Val Lys Val Val His Thr Ser Asn Asn Val Ala Gly Gln Val Tyr
        410                 415                 420 atc ccc gaa atc aac tgg att ctt atg gtt ctc tgc ctc tgc gtc aca    1409
Ile Pro Glu Ile Asn Trp Ile Leu Met Val Leu Cys Leu Cys Val Thr
    425                 430                 435 gct ggt ttc cga gac acg gac caa atc gga aat gct tac ggt atc gcc    1457
Ala Gly Phe Arg Asp Thr Asp Gln Ile Gly Asn Ala Tyr Gly Ile Ala
440             445                 450                 455 gtg gtg atg gtc atg atc gtc acc acc ctg atg acc cta gtg ata        1505
Val Val Met Val Met Ile Val Thr Thr Leu Leu Met Thr Leu Val Ile
                460                 465                 470 atc atc att tgg cgg aag cac ttc ctc ctt gcc ttg cta ttc ctt gtc    1553
Ile Ile Ile Trp Arg Lys His Phe Leu Leu Ala Leu Leu Phe Leu Val
            475                 480                 485 gtg ttc gca tca atc gag gga att tat gtc agt gcg gtc cta ttc aag    1601
Val Phe Ala Ser Ile Glu Gly Ile Tyr Val Ser Ala Val Leu Phe Lys
        490                 495                 500 aca act caa gga ggc tgg gtg ccg ctg gtc att tcg gtg gtc ttc ggc    1649
Thr Thr Gln Gly Gly Trp Val Pro Leu Val Ile Ser Val Val Phe Gly
    505                 510                 515 aca gtc atg ggc aca tgg cat tac gga acc ttg aaa cgc tac cag tat    1697
Thr Val Met Gly Thr Trp His Tyr Gly Thr Leu Lys Arg Tyr Gln Tyr
520             525                 530                 535 gag atg cag cac aag gtt tca gtg gga tgg ttg ctt ggg ctt gga cct    1745
Glu Met Gln His Lys Val Ser Val Gly Trp Leu Leu Gly Leu Gly Pro
                540                 545                 550 agc ctc ggc ctc gtt cgt gtc ccc gga atc ggt ctc atg tac aca gat    1793
Ser Leu Gly Leu Val Arg Val Pro Gly Ile Gly Leu Met Tyr Thr Asp
            555                 560                 565 ctc gct cat gga gtg ccg ccg cta ttc tcg cat ttc atc acc aat ctc    1841
Leu Ala His Gly Val Pro Pro Leu Phe Ser His Phe Ile Thr Asn Leu
        570                 575                 580 ccc gcc atc cat tcc acc gta gtc ttc gtc tgc gtt aaa tac ctg cca    1889
Pro Ala Ile His Ser Thr Val Val Phe Val Cys Val Lys Tyr Leu Pro
    585                 590                 595 gtg aac acg gta cca caa gat gag aga ttt cta atc cgt cgc atc ggt    1937
Val Asn Thr Val Pro Gln Asp Glu Arg Phe Leu Ile Arg Arg Ile Gly
600             605                 610                 615 tca aga gct tat tcc atg tac cgt tgt gca gca cgt tac ggc tac ata    1985
Ser Arg Ala Tyr Ser Met Tyr Arg Cys Ala Ala Arg Tyr Gly Tyr Ile
                620                 625                 630 gac ctc cac aag aaa gat gac aac ttc gag caa ctg cta att caa agc    2033
Asp Leu His Lys Lys Asp Asp Asn Phe Glu Gln Leu Leu Ile Gln Ser
            635                 640                 645 tta atc agt ttc gtc gag att gag tct atg aga gag agc tca ggc cgg    2081
Leu Ile Ser Phe Val Glu Ile Glu Ser Met Arg Glu Ser Ser Gly Arg
        650                 655                 660
```

```
gag tcc atg gct gca agc tgg acc cca gat caa cag ccg atg gag gag     2129
Glu Ser Met Ala Ala Ser Trp Thr Pro Asp Gln Gln Pro Met Glu Glu
665                 670                 675 gcc acg gtg cca act acg tcg acg atc act cca aac cgg ctt cag ttg     2177
Ala Thr Val Pro Thr Thr Ser Thr Ile Thr Pro Asn Arg Leu Gln Leu
680                 685                 690                 695 caa aga atg ctg aga tta cac agt ctg atg ggc gga ggc aac agc gtc     2225
Gln Arg Met Leu Arg Leu His Ser Leu Met Gly Gly Gly Asn Ser Val
            700                 705                 710 ggc gac ggt tat tcc act cag tac tcc cag acc gcc tcg aac tcg gtc     2273
Gly Asp Gly Tyr Ser Thr Gln Tyr Ser Gln Thr Ala Ser Asn Ser Val
            715                 720                 725 gag atg tct gct aac cag gaa tgc agt att cca aac ctg agc gtc aac     2321
Glu Met Ser Ala Asn Gln Glu Cys Ser Ile Pro Asn Leu Ser Val Asn
730                 735                 740 ggc agc aac agc agc agc agc ccg cat ccg caa gac gaa gtt gcc ttc     2369
Gly Ser Asn Ser Ser Ser Ser Pro His Pro Gln Asp Glu Val Ala Phe
745                 750                 755 ctg aat gca tgc aaa gat gct ggc gtg gtg tac ata ctc ggt aac aac     2417
Leu Asn Ala Cys Lys Asp Ala Gly Val Val Tyr Ile Leu Gly Asn Asn
760                 765                 770                 775 atc gtg aaa gcg aga aag gat gca gga ttt ttc aag aag ctg gtg atc     2465
Ile Val Lys Ala Arg Lys Asp Ala Gly Phe Phe Lys Lys Leu Val Ile
            780                 785                 790 aac tac atg tat acc ttt ctg cga agg ata agc cga gac agc agc gtg     2513
Asn Tyr Met Tyr Thr Phe Leu Arg Arg Ile Ser Arg Asp Ser Ser Val
            795                 800                 805 gtg ctc aac atc ccg cac gag tgc cta ctt cat gtc ggc atg gtg tac     2561
Val Leu Asn Ile Pro His Glu Cys Leu Leu His Val Gly Met Val Tyr
            810                 815                 820 tat gtt tgattcttt gggtctgagt tttgtacagg gcgacgttaa cgc               2610
Tyr Val
825

<210> SEQ ID NO 2
<211> LENGTH: 825
<212> TYPE: PRT
<213> ORGANISM: Physcomitrella patens

<400> SEQUENCE: 2

Met Ser Thr Thr Thr Val Ser Glu Asp Ala Glu Asp Gly Arg Gly Gly
1               5                   10                  15

Arg Asn Gly Gln Gln Ala Asn Gln Gly Arg Leu Trp Asp Met Asp Gln
            20                  25                  30

Arg Ile Asp Gln Pro Leu Gly Ala Glu Ala Asp His Val Arg Ser Met
        35                  40                  45

Tyr Arg Asp Gln Thr Met Pro Pro Ser Val Val Leu Cys Leu Ala Phe
    50                  55                  60

Gln Ser Leu Gly Val Val Tyr Gly Asp Leu Gly Thr Ser Pro Leu Tyr
65                  70                  75                  80

Val Phe Lys Ser Thr Phe Ala Asn Gly Gly Val Arg Asn Glu Asp Asp
                85                  90                  95

Ile Ile Gly Ala Leu Ser Leu Ile Ile Tyr Thr Leu Thr Ile Ile Pro
            100                 105                 110

Leu Ile Lys Tyr Val Phe Ile Val Leu Arg Ala Asn Asp Asn Gly Glu
        115                 120                 125

Gly Gly Ser Phe Ala Leu Tyr Ser Leu Leu Cys Arg Tyr Cys Asn Ile
    130                 135                 140
```

```
Ser Ala Leu Pro Asn Gln His Pro Ser Asp Ala Glu Leu Thr Thr Tyr
145                 150                 155                 160

Val Val Asp Asn Ala Arg Arg Lys Thr Trp Ile Gln Arg Lys Leu Glu
            165                 170                 175

Ser Ser Val Leu Ala Gln Gln Val Leu Leu Val Ile Val Leu Phe Gly
        180                 185                 190

Thr Cys Met Val Ile Gly Asp Gly Ile Leu Thr Pro Ser Ile Ser Val
    195                 200                 205

Leu Ser Ala Val Val Gly Ile Lys Ala Ser Ser Ser Leu Asp Thr
210                 215                 220

Asn Leu Val Thr Gly Ile Ser Cys Val Ile Leu Val Ile Leu Phe Ser
225                 230                 235                 240

Val Gln Arg Phe Gly Thr Ala Lys Ile Ser Val Leu Phe Ala Pro Ile
            245                 250                 255

Phe Leu Val Trp Phe Leu Ser Leu Ala Cys Ile Gly Cys Tyr Asn Ile
            260                 265                 270

Ile Lys Trp Glu Lys Ser Ile Phe Leu Ala Phe Asn Pro Leu Gln Ile
        275                 280                 285

Val His Phe Phe Arg Arg Asn Gly Arg Gln Gly Trp Glu His Leu Gly
290                 295                 300

Gly Ile Val Leu Cys Met Thr Gly Thr Glu Ala Leu Phe Ala Asp Leu
305                 310                 315                 320

Gly His Phe Ser Cys Arg Ser Ile Gln Ile Val Phe Thr Ser Leu Val
            325                 330                 335

Tyr Pro Cys Leu Phe Leu Thr Tyr Leu Gly Gln Ala Ala Tyr Leu Val
            340                 345                 350

Glu His Met Glu Asp Val Asn Asp Pro Phe Tyr Ser Ser Leu Pro Ser
            355                 360                 365

Ser Ile Tyr Trp Pro Ile Phe Val Leu Ala Thr Ile Ser Ala Met Ile
        370                 375                 380

Ala Ser Arg Ala Met Ile Ser Ala Thr Phe Ser Ile Val Lys Gln Ala
385                 390                 395                 400

Thr Ala Leu Gly Cys Phe Pro Arg Val Lys Val Val His Thr Ser Asn
            405                 410                 415

Asn Val Ala Gly Gln Val Tyr Ile Pro Glu Ile Asn Trp Ile Leu Met
            420                 425                 430

Val Leu Cys Leu Cys Val Thr Ala Gly Phe Arg Asp Thr Asp Gln Ile
            435                 440                 445

Gly Asn Ala Tyr Gly Ile Ala Val Val Met Val Met Ile Val Thr Thr
450                 455                 460

Leu Leu Met Thr Leu Val Ile Ile Ile Trp Arg Lys His Phe Leu
465                 470                 475                 480

Leu Ala Leu Leu Phe Leu Val Val Phe Ala Ser Ile Glu Gly Ile Tyr
            485                 490                 495

Val Ser Ala Val Leu Phe Lys Thr Thr Gln Gly Gly Trp Val Pro Leu
            500                 505                 510

Val Ile Ser Val Val Phe Gly Thr Val Met Gly Thr Trp His Tyr Gly
            515                 520                 525

Thr Leu Lys Arg Tyr Gln Tyr Glu Met Gln His Lys Val Ser Val Gly
            530                 535                 540

Trp Leu Leu Gly Leu Gly Pro Ser Leu Gly Leu Val Arg Val Pro Gly
545                 550                 555                 560

Ile Gly Leu Met Tyr Thr Asp Leu Ala His Gly Val Pro Pro Leu Phe
            565                 570                 575
```

```
Ser His Phe Ile Thr Asn Leu Pro Ala Ile His Ser Thr Val Val Phe
        580                 585                 590

Val Cys Val Lys Tyr Leu Pro Val Asn Thr Val Pro Gln Asp Glu Arg
        595                 600                 605

Phe Leu Ile Arg Arg Ile Gly Ser Arg Ala Tyr Ser Met Tyr Arg Cys
        610                 615                 620

Ala Ala Arg Tyr Gly Tyr Ile Asp Leu His Lys Lys Asp Asn Phe
625                 630                 635                 640

Glu Gln Leu Leu Ile Gln Ser Leu Ile Ser Phe Val Glu Ile Glu Ser
                645                 650                 655

Met Arg Glu Ser Ser Gly Arg Glu Ser Met Ala Ala Ser Trp Thr Pro
                660                 665                 670

Asp Gln Gln Pro Met Glu Glu Ala Thr Val Pro Thr Thr Ser Thr Ile
                675                 680                 685

Thr Pro Asn Arg Leu Gln Leu Gln Arg Met Leu Arg Leu His Ser Leu
                690                 695                 700

Met Gly Gly Gly Asn Ser Val Gly Asp Gly Tyr Ser Thr Gln Tyr Ser
705                 710                 715                 720

Gln Thr Ala Ser Asn Ser Val Glu Met Ser Ala Asn Gln Glu Cys Ser
                725                 730                 735

Ile Pro Asn Leu Ser Val Asn Gly Ser Asn Ser Ser Ser Pro His
                740                 745                 750

Pro Gln Asp Glu Val Ala Phe Leu Asn Ala Cys Lys Asp Ala Gly Val
                755                 760                 765

Val Tyr Ile Leu Gly Asn Asn Ile Val Lys Ala Arg Lys Asp Ala Gly
                770                 775                 780

Phe Phe Lys Lys Leu Val Ile Asn Tyr Met Tyr Thr Phe Leu Arg Arg
785                 790                 795                 800

Ile Ser Arg Asp Ser Ser Val Val Leu Asn Ile Pro His Glu Cys Leu
                805                 810                 815

Leu His Val Gly Met Val Tyr Tyr Val
                820                 825

<210> SEQ ID NO 3
<211> LENGTH: 2852
<212> TYPE: DNA
<213> ORGANISM: Glycine max
<220> FEATURE:
<221> NAME/KEY: CDS
<222> LOCATION: (166)..(2628)
<223> OTHER INFORMATION: GmAKT-2 (GM59666231)

<400> SEQUENCE: 3
attaaaggaa tcatccaaag ggaactcaaa atgaaatgaa atggaaatgt aagaagtagt      60
actgaaaact gaactcaact aactcgtgac tcgtcagaga gaagaaaaga atatcgttcg     120
ttcgctctta ccttcttcac cttccttcct ctctctctct agaga atg gaa ccg gaa    177
                                                  Met Glu Pro Glu
                                                    1 tcc gga act tcg act tct cgg aat cct tct cag ttg tct tgg gtg aat      225
Ser Gly Thr Ser Thr Ser Arg Asn Pro Ser Gln Leu Ser Trp Val Asn
  5                  10                  15                  20 ctg tct agg aat tta tta tta gcg tat caa agc ttt ggt gtg gtg tat      273
Leu Ser Arg Asn Leu Leu Leu Ala Tyr Gln Ser Phe Gly Val Val Tyr
                 25                  30                  35 gga gat ctg agc act tct cct ctc tat gtc ttc aca agc acc ttc aag      321
Gly Asp Leu Ser Thr Ser Pro Leu Tyr Val Phe Thr Ser Thr Phe Lys
             40                  45                  50
```

```
ggg aag ttg cag aat cac cat gac gag gaa act ata ttc ggc acg ttt      369
Gly Lys Leu Gln Asn His His Asp Glu Glu Thr Ile Phe Gly Thr Phe
            55                  60                  65 tcg ttg att ttt tgg acc ctt act ttg att ccg ttg ctt aag tat gta      417
Ser Leu Ile Phe Trp Thr Leu Thr Leu Ile Pro Leu Leu Lys Tyr Val
        70                  75                  80 ttc atc cta ttg agt gct gat gac aac ggg gaa ggt gga aca ttc gct      465
Phe Ile Leu Leu Ser Ala Asp Asp Asn Gly Glu Gly Gly Thr Phe Ala
 85                 90                  95                 100 ctt tat tcg ctg ctc tgt agg cat gcc aag ttt aat ttg ctc ccc aat      513
Leu Tyr Ser Leu Leu Cys Arg His Ala Lys Phe Asn Leu Leu Pro Asn
                105                 110                 115 caa caa gca gct gat gag gag tta tca tcc tat aaa tat ggt ccc tct      561
Gln Gln Ala Ala Asp Glu Glu Leu Ser Ser Tyr Lys Tyr Gly Pro Ser
            120                 125                 130 tca cag gct ata gcc tct tct cct cta aag agg ttt ctg gag aaa cat      609
Ser Gln Ala Ile Ala Ser Ser Pro Leu Lys Arg Phe Leu Glu Lys His
        135                 140                 145 aaa agg tta aga aca gcc ctg ctt gtt gtg gta ttt ttt ggt gct tgc      657
Lys Arg Leu Arg Thr Ala Leu Leu Val Val Val Leu Phe Gly Ala Cys
150                 155                 160 atg gtc att ggt gat ggt gtg ctt act cca gca att tcg gtt cta gca      705
Met Val Ile Gly Asp Gly Val Leu Thr Pro Ala Ile Ser Val Leu Ala
165                 170                 175                 180 tca gtc tca gga cta aaa gtt aca gaa aaa aaa tta aca gat ggt gag      753
Ser Val Ser Gly Leu Lys Val Thr Glu Lys Lys Leu Thr Asp Gly Glu
                185                 190                 195 cca aat ctc att tat tcc ttt ttt ttt gtt ctc atc att gct ttt gtt      801
Pro Asn Leu Ile Tyr Ser Phe Phe Phe Val Leu Ile Ile Ala Phe Val
            200                 205                 210 atg cta agg gca aat tgg ttg cag gtg aac ttg aga aat ttc atg ttg      849
Met Leu Arg Ala Asn Trp Leu Gln Val Asn Leu Arg Asn Phe Met Leu
        215                 220                 225 ttt gca ggt gaa ctt gtc ctg ctt gcc tgt gtc ata ttg gtt gga ctg      897
Phe Ala Gly Glu Leu Val Leu Leu Ala Cys Val Ile Leu Val Gly Leu
                230                 235                 240 ttt gct ctc caa cat tgt ggc aca cac aaa gtt gca gtt atg ttt gca      945
Phe Ala Leu Gln His Cys Gly Thr His Lys Val Ala Val Met Phe Ala
245                 250                 255                 260 cca att gta ata atc tgg ctt gta tca ata ttt tct att ggg gtg tat      993
Pro Ile Val Ile Ile Trp Leu Val Ser Ile Phe Ser Ile Gly Val Tyr
                265                 270                 275 aat aca att cat tgg aat cca aaa ata gtc cgt gct ata tcg cca tat     1041
Asn Thr Ile His Trp Asn Pro Lys Ile Val Arg Ala Ile Ser Pro Tyr
            280                 285                 290 tat atc atc aag ttt ttt agc agg act ggt aaa gaa ggt tgg gtt tct     1089
Tyr Ile Ile Lys Phe Phe Ser Arg Thr Gly Lys Glu Gly Trp Val Ser
        295                 300                 305 ctt gga ggg ata ctt ctt tgt atc act gga act gaa gct atg ttt gcg     1137
Leu Gly Gly Ile Leu Leu Cys Ile Thr Gly Thr Glu Ala Met Phe Ala
310                 315                 320 gat ctt ggt cat ttc act gct tcg tca ata agg ctt gca ttt gcg         1185
Asp Leu Gly His Phe Thr Ala Ser Ser Ile Arg Leu Ala Phe Ala Phe
325                 330                 335                 340 gtt ata tac ccg tgt tta gtg gta cag tat atg ggt caa gct gct ttc     1233
Val Ile Tyr Pro Cys Leu Val Val Gln Tyr Met Gly Gln Ala Ala Phe
                345                 350                 355 ttg tct aaa aat ctc gac tct gtt gat aac ggt ttt tat gac tca ata     1281
Leu Ser Lys Asn Leu Asp Ser Val Asp Asn Gly Phe Tyr Asp Ser Ile
            360                 365                 370
```

| | | |
|---|---|---|
| cct gac cct gtg ttt tgg cct gtt ttc ata atc gcc acc ctt gct gca<br>Pro Asp Pro Val Phe Trp Pro Val Phe Ile Ile Ala Thr Leu Ala Ala<br>     375                      380                   385 | 1329 |
| att gtt ggg agt caa gct gtt ata act gca act ttc tcc atc atc aag<br>Ile Val Gly Ser Gln Ala Val Ile Thr Ala Thr Phe Ser Ile Ile Lys<br>390                      395                      400 | 1377 |
| cag tgt cat gcg ctt ggt tgc ttt ccg cga gtc aaa gtt gta cac acc<br>Gln Cys His Ala Leu Gly Cys Phe Pro Arg Val Lys Val Val His Thr<br>405                      410                      415                   420 | 1425 |
| tca aaa cat ata tat gga cag atc tat atc cca gaa atc aat tgg ata<br>Ser Lys His Ile Tyr Gly Gln Ile Tyr Ile Pro Glu Ile Asn Trp Ile<br>                     425                      430                      435 | 1473 |
| ctt atg atc cta act ctt gca ata acc att gga ttt cag gac acg acc<br>Leu Met Ile Leu Thr Leu Ala Ile Thr Ile Gly Phe Gln Asp Thr Thr<br>440                      445                      450 | 1521 |
| ata att gga aat gct tat ggg ttg gct tgt atg aca gtt atg ttc ata<br>Ile Ile Gly Asn Ala Tyr Gly Leu Ala Cys Met Thr Val Met Phe Ile<br>                     455                      460                      465 | 1569 |
| act aca ttt ctg atg aca cta gtc gca atc ttt gtc tgg cag aaa agt<br>Thr Thr Phe Leu Met Thr Leu Val Ala Ile Phe Val Trp Gln Lys Ser<br>470                      475                      480 | 1617 |
| gtc ttg att gct gtt gta ttt ctt tta ttc ctt tgg gtg ata gag ggc<br>Val Leu Ile Ala Val Val Phe Leu Leu Phe Leu Trp Val Ile Glu Gly<br>485                      490                      495                      500 | 1665 |
| gta tat cta tca gca gct ttc atc aaa gtg cct cag gga gga tgg gta<br>Val Tyr Leu Ser Ala Ala Phe Ile Lys Val Pro Gln Gly Gly Trp Val<br>                     505                      510                      515 | 1713 |
| cct cta gtc tta tca ttc atc ttc atg att gtt atg tac gtg tgg cat<br>Pro Leu Val Leu Ser Phe Ile Phe Met Ile Val Met Tyr Val Trp His<br>                 520                      525                      530 | 1761 |
| tat gga act cgt agg aag tac agc tat gat ctg cac aac aaa gtt tca<br>Tyr Gly Thr Arg Arg Lys Tyr Ser Tyr Asp Leu His Asn Lys Val Ser<br>            535                      540                      545 | 1809 |
| ttg aaa tgg tta ctg ggc ttg ggc cca agc ctt ggc att gtt cgt gta<br>Leu Lys Trp Leu Leu Gly Leu Gly Pro Ser Leu Gly Ile Val Arg Val<br>550                      555                      560 | 1857 |
| cct ggg att ggt ctc atc tac act gaa ctg gca aca ggc ata cct gca<br>Pro Gly Ile Gly Leu Ile Tyr Thr Glu Leu Ala Thr Gly Ile Pro Ala<br>565                      570                      575                      580 | 1905 |
| ata ttt tcc cat ttt gta aca aat ctt cct gca ttt cac cag gtg ttg<br>Ile Phe Ser His Phe Val Thr Asn Leu Pro Ala Phe His Gln Val Leu<br>                     585                      590                      595 | 1953 |
| gtt ttt gtt tgt gta aaa tca gtt cct gtt cca tat gtt tca ccg gaa<br>Val Phe Val Cys Val Lys Ser Val Pro Val Pro Tyr Val Ser Pro Glu<br>                 600                      605                      610 | 2001 |
| gaa cgt ttc ctt att ggg cga gtt tgc ccc aga cca tat cga atg tat<br>Glu Arg Phe Leu Ile Gly Arg Val Cys Pro Arg Pro Tyr Arg Met Tyr<br>            615                      620                      625 | 2049 |
| agg tgc att gtc aga tat ggt tac aag gac att caa agg gat gat gga<br>Arg Cys Ile Val Arg Tyr Gly Tyr Lys Asp Ile Gln Arg Asp Asp Gly<br>630                      635                      640 | 2097 |
| gat ttt gag aat cat ctt ata cag agt ata gca gaa ttt atc caa atg<br>Asp Phe Glu Asn His Leu Ile Gln Ser Ile Ala Glu Phe Ile Gln Met<br>645                      650                      655                      660 | 2145 |
| gaa gca gtg caa cct cag ttc tca agt tcc gaa gct tct tct tca ctt<br>Glu Ala Val Gln Pro Gln Phe Ser Ser Ser Glu Ala Ser Ser Ser Leu<br>                     665                      670                      675 | 2193 |
| gat ggg agg atg gcc gtt ata agt tct aga aac tat gat tat gct tca<br>Asp Gly Arg Met Ala Val Ile Ser Ser Arg Asn Tyr Asp Tyr Ala Ser<br>                     680                      685                      690 | 2241 |

-continued

```
agt tta ata gtt tct gag cag gag gat ata ggc gtt gac ata tcc atc    2289
Ser Leu Ile Val Ser Glu Gln Glu Asp Ile Gly Val Asp Ile Ser Ile
        695                 700                 705 cct agc agc aga tct gca acc ctg caa agt ttg caa tcg gtt tac gac    2337
Pro Ser Ser Arg Ser Ala Thr Leu Gln Ser Leu Gln Ser Val Tyr Asp
710                 715                 720 gat gaa act ccg caa gtt aga aga cga gta aga ttt cag cta cca        2385
Asp Glu Thr Pro Gln Val Arg Arg Arg Val Arg Phe Gln Leu Pro
725                 730                 735                 740 gaa aac act ggt atg gat ccc gat gtt agg gaa gag ctt ttg gat tta    2433
Glu Asn Thr Gly Met Asp Pro Asp Val Arg Glu Glu Leu Leu Asp Leu
                745                 750                 755 att caa gcc aag gaa gct ggg gtt gca tat ata atg ggg cac tca tat    2481
Ile Gln Ala Lys Glu Ala Gly Val Ala Tyr Ile Met Gly His Ser Tyr
            760                 765                 770 gtg aag gca agg aaa tca tcc tca ttc ttg aaa aag ctc gtg att gat    2529
Val Lys Ala Arg Lys Ser Ser Ser Phe Leu Lys Lys Leu Val Ile Asp
        775                 780                 785 att ggt tac tca ttt ctg cgc aag aat tgc agg ggt cca gct gta gct    2577
Ile Gly Tyr Ser Phe Leu Arg Lys Asn Cys Arg Gly Pro Ala Val Ala
    790                 795                 800 ctt aac att cct cac att agt ctt att gaa gtt ggg atg ata tat tat    2625
Leu Asn Ile Pro His Ile Ser Leu Ile Glu Val Gly Met Ile Tyr Tyr
805                 810                 815                 820 gtg tagttattgg tgaaatttac aacttgatcc tagttgcata ggtaattaat        2678
Val tgtagctcac gggaaaatga gtgtcttttg gggctacgtg tttatctttg ctttcgcatc  2738
tctctcccaa tgtaattaca tagttgcaac aataaggttt tagaattata tttaggaatc  2798
agaatatttt cctcaaaaaa aaaaaaaaaa aagcgagaga gagaccgaca cgca         2852

<210> SEQ ID NO 4
<211> LENGTH: 821
<212> TYPE: PRT
<213> ORGANISM: Glycine max

<400> SEQUENCE: 4

Met Glu Pro Glu Ser Gly Thr Ser Thr Ser Arg Asn Pro Ser Gln Leu
1               5                   10                  15

Ser Trp Val Asn Leu Ser Arg Asn Leu Leu Ala Tyr Gln Ser Phe
            20                  25                  30

Gly Val Val Tyr Gly Asp Leu Ser Thr Ser Pro Leu Tyr Val Phe Thr
        35                  40                  45

Ser Thr Phe Lys Gly Lys Leu Gln Asn His His Asp Glu Glu Thr Ile
    50                  55                  60

Phe Gly Thr Phe Ser Leu Ile Phe Trp Thr Leu Thr Leu Ile Pro Leu
65                  70                  75                  80

Leu Lys Tyr Val Phe Ile Leu Leu Ser Ala Asp Asp Asn Gly Glu Gly
                85                  90                  95

Gly Thr Phe Ala Leu Tyr Ser Leu Leu Cys Arg His Ala Lys Phe Asn
            100                 105                 110

Leu Leu Pro Asn Gln Gln Ala Ala Asp Glu Glu Leu Ser Ser Tyr Lys
        115                 120                 125

Tyr Gly Pro Ser Ser Gln Ala Ile Ala Ser Ser Pro Leu Lys Arg Phe
    130                 135                 140

Leu Glu Lys His Lys Arg Leu Arg Thr Ala Leu Leu Val Val Val Leu
145                 150                 155                 160
```

```
Phe Gly Ala Cys Met Val Ile Gly Asp Gly Val Leu Thr Pro Ala Ile
                165                 170                 175

Ser Val Leu Ala Ser Val Ser Gly Leu Lys Val Thr Glu Lys Lys Leu
            180                 185                 190

Thr Asp Gly Glu Pro Asn Leu Ile Tyr Ser Phe Phe Val Leu Ile
        195                 200                 205

Ile Ala Phe Val Met Leu Arg Ala Asn Trp Leu Gln Val Asn Leu Arg
    210                 215                 220

Asn Phe Met Leu Phe Ala Gly Glu Leu Val Leu Leu Ala Cys Val Ile
225                 230                 235                 240

Leu Val Gly Leu Phe Ala Leu Gln His Cys Gly Thr His Lys Val Ala
                245                 250                 255

Val Met Phe Ala Pro Ile Val Ile Ile Trp Leu Val Ser Ile Phe Ser
                260                 265                 270

Ile Gly Val Tyr Asn Thr Ile His Trp Asn Pro Lys Ile Val Arg Ala
            275                 280                 285

Ile Ser Pro Tyr Tyr Ile Ile Lys Phe Phe Ser Arg Thr Gly Lys Glu
        290                 295                 300

Gly Trp Val Ser Leu Gly Gly Ile Leu Leu Cys Ile Thr Gly Thr Glu
305                 310                 315                 320

Ala Met Phe Ala Asp Leu Gly His Phe Thr Ala Ser Ser Ile Arg Leu
                325                 330                 335

Ala Phe Ala Phe Val Ile Tyr Pro Cys Leu Val Val Gln Tyr Met Gly
                340                 345                 350

Gln Ala Ala Phe Leu Ser Lys Asn Leu Asp Ser Val Asp Asn Gly Phe
                355                 360                 365

Tyr Asp Ser Ile Pro Asp Pro Val Phe Trp Pro Val Phe Ile Ile Ala
        370                 375                 380

Thr Leu Ala Ala Ile Val Gly Ser Gln Ala Val Ile Thr Ala Thr Phe
385                 390                 395                 400

Ser Ile Ile Lys Gln Cys His Ala Leu Gly Cys Phe Pro Arg Val Lys
                405                 410                 415

Val Val His Thr Ser Lys His Ile Tyr Gly Gln Ile Tyr Ile Pro Glu
                420                 425                 430

Ile Asn Trp Ile Leu Met Ile Leu Thr Leu Ala Ile Thr Ile Gly Phe
        435                 440                 445

Gln Asp Thr Thr Ile Ile Gly Asn Ala Tyr Gly Leu Ala Cys Met Thr
        450                 455                 460

Val Met Phe Ile Thr Thr Phe Leu Met Thr Leu Val Ala Ile Phe Val
465                 470                 475                 480

Trp Gln Lys Ser Val Leu Ile Ala Val Val Phe Leu Leu Phe Leu Trp
                485                 490                 495

Val Ile Glu Gly Val Tyr Leu Ser Ala Ala Phe Ile Lys Val Pro Gln
            500                 505                 510

Gly Gly Trp Val Pro Leu Val Leu Ser Phe Ile Phe Met Ile Val Met
            515                 520                 525

Tyr Val Trp His Tyr Gly Thr Arg Arg Lys Tyr Ser Tyr Asp Leu His
            530                 535                 540

Asn Lys Val Ser Leu Lys Trp Leu Leu Gly Leu Gly Pro Ser Leu Gly
545                 550                 555                 560

Ile Val Arg Val Pro Gly Ile Gly Leu Ile Tyr Thr Glu Leu Ala Thr
                565                 570                 575

Gly Ile Pro Ala Ile Phe Ser His Phe Val Thr Asn Leu Pro Ala Phe
                580                 585                 590
```

```
His Gln Val Leu Val Phe Val Cys Val Lys Ser Val Pro Val Pro Tyr
            595                 600                 605

Val Ser Pro Glu Glu Arg Phe Leu Ile Gly Arg Val Cys Pro Arg Pro
    610                 615                 620

Tyr Arg Met Tyr Arg Cys Ile Val Arg Tyr Gly Tyr Lys Asp Ile Gln
625                 630                 635                 640

Arg Asp Asp Gly Asp Phe Glu Asn His Leu Ile Gln Ser Ile Ala Glu
                645                 650                 655

Phe Ile Gln Met Glu Ala Val Gln Pro Gln Phe Ser Ser Glu Ala
                660                 665                 670

Ser Ser Ser Leu Asp Gly Arg Met Ala Val Ile Ser Ser Arg Asn Tyr
        675                 680                 685

Asp Tyr Ala Ser Ser Leu Ile Val Ser Glu Gln Glu Asp Ile Gly Val
        690                 695                 700

Asp Ile Ser Ile Pro Ser Ser Arg Ser Ala Thr Leu Gln Ser Leu Gln
705                 710                 715                 720

Ser Val Tyr Asp Asp Glu Thr Pro Gln Val Arg Arg Arg Val Arg
                725                 730                 735

Phe Gln Leu Pro Glu Asn Thr Gly Met Asp Pro Asp Val Arg Glu Glu
                740                 745                 750

Leu Leu Asp Leu Ile Gln Ala Lys Glu Ala Gly Val Ala Tyr Ile Met
            755                 760                 765

Gly His Ser Tyr Val Lys Ala Arg Lys Ser Ser Phe Leu Lys Lys
        770                 775                 780

Leu Val Ile Asp Ile Gly Tyr Ser Phe Leu Arg Lys Asn Cys Arg Gly
785                 790                 795                 800

Pro Ala Val Ala Leu Asn Ile Pro His Ile Ser Leu Ile Glu Val Gly
                805                 810                 815

Met Ile Tyr Tyr Val
            820

<210> SEQ ID NO 5
<211> LENGTH: 2794
<212> TYPE: DNA
<213> ORGANISM: Triticum aestivum
<220> FEATURE:
<221> NAME/KEY: CDS
<222> LOCATION: (32)..(2386)
<223> OTHER INFORMATION: TaAKT-1 (TA 59824966)

<400> SEQUENCE: 5
gtgagagaga gatcatcatc gtaccttgac g atg gct gag cct ctg aag gca        52
                                  Met Ala Glu Pro Leu Lys Ala
                                   1               5 aac ggc aat gga gct gcc gaa ggg ggt gct gcg ggc tct gcg ttt gca      100
Asn Gly Asn Gly Ala Ala Glu Gly Gly Ala Ala Gly Ser Ala Phe Ala
         10                  15                  20 tcg gtg aag gtg ccg ccg tcg ccg cca agg agg ctg cag agg ttc gac      148
Ser Val Lys Val Pro Pro Ser Pro Pro Arg Arg Leu Gln Arg Phe Asp
 25                  30                  35 tcc ctg cat atg gag gcc ggg aag att cct ggt ggc cac agc tat gca      196
Ser Leu His Met Glu Ala Gly Lys Ile Pro Gly Gly His Ser Tyr Ala
40                  45                  50                  55 gcc aag gtt ggc tgg gcg acg aca ctg cac ttg gcc ttc cag agc cta      244
Ala Lys Val Gly Trp Ala Thr Thr Leu His Leu Ala Phe Gln Ser Leu
                 60                  65                  70 ggt gtg gtt tat ggg gac atg gga act tca ccc ctc tat gtg ttc tcc      292
Gly Val Val Tyr Gly Asp Met Gly Thr Ser Pro Leu Tyr Val Phe Ser
```

-continued

```
                75                  80                  85
agc acc ttt act ggt ggg atc aag gac aca gat gac ctc ctt ggt gtc    340
Ser Thr Phe Thr Gly Gly Ile Lys Asp Thr Asp Asp Leu Leu Gly Val
         90                  95                 100 atg tcc ttg ata atc tat act gta ctt ctc ctt cca ttg atg aaa tat    388
Met Ser Leu Ile Ile Tyr Thr Val Leu Leu Leu Pro Leu Met Lys Tyr
    105                 110                 115 tgt ttc att gtc ttg aga gct aat gac aac ggc gat ggc gga aca ttt    436
Cys Phe Ile Val Leu Arg Ala Asn Asp Asn Gly Asp Gly Gly Thr Phe
120                 125                 130                 135 gca ctt tat tcc ttg ata tct cgg tat gct agg att agc ttg ata cca    484
Ala Leu Tyr Ser Leu Ile Ser Arg Tyr Ala Arg Ile Ser Leu Ile Pro
             140                 145                 150 aac cag cag gct gaa gat gca aca gtc tct cac tac aag tta gag tcc    532
Asn Gln Gln Ala Glu Asp Ala Thr Val Ser His Tyr Lys Leu Glu Ser
                 155                 160                 165 cct acg aat cgt gtc aag cgg gct cat tgg att aag gaa aag atg gaa    580
Pro Thr Asn Arg Val Lys Arg Ala His Trp Ile Lys Glu Lys Met Glu
         170                 175                 180 aac agc ccg aaa ttt aag gtc ata ctt ttc cta gtg aca att cta gca    628
Asn Ser Pro Lys Phe Lys Val Ile Leu Phe Leu Val Thr Ile Leu Ala
    185                 190                 195 aca tca atg gtt att ggt gac ggt gtg cta act cca tgt att tca gtg    676
Thr Ser Met Val Ile Gly Asp Gly Val Leu Thr Pro Cys Ile Ser Val
200                 205                 210                 215 ctt agt gca gtt acg gga atc aag caa tca gca aag tcg tta act caa    724
Leu Ser Ala Val Thr Gly Ile Lys Gln Ser Ala Lys Ser Leu Thr Gln
             220                 225                 230 gga caa att gct ggc atc gca atc ggc att ctg atc gcc ctc ttt ctt    772
Gly Gln Ile Ala Gly Ile Ala Ile Gly Ile Leu Ile Ala Leu Phe Leu
                 235                 240                 245 gtc cag cgc ttt ggc aca gac aaa gtt ggt tac aca ttt ggc cca gta    820
Val Gln Arg Phe Gly Thr Asp Lys Val Gly Tyr Thr Phe Gly Pro Val
         250                 255                 260 atc ttt ata tgg ttc atc tta att gcc ggc att gga att tat aat ttg    868
Ile Phe Ile Trp Phe Ile Leu Ile Ala Gly Ile Gly Ile Tyr Asn Leu
    265                 270                 275 atc aaa cat gat act gga att ctg aaa gca ttc aac cca caa tac ata    916
Ile Lys His Asp Thr Gly Ile Leu Lys Ala Phe Asn Pro Gln Tyr Ile
280                 285                 290                 295 gtg gaa tat ttc caa aga aat ggg aag gac ggc tgg att tcg ctt gga    964
Val Glu Tyr Phe Gln Arg Asn Gly Lys Asp Gly Trp Ile Ser Leu Gly
             300                 305                 310 ggt gtt atc tta tgc att aca gga acc gaa gca atg ttt gct gac ctt   1012
Gly Val Ile Leu Cys Ile Thr Gly Thr Glu Ala Met Phe Ala Asp Leu
                 315                 320                 325 ggt cac ttc aat gtg aga gca att cag att ggc ctt tct gca gtt ctg   1060
Gly His Phe Asn Val Arg Ala Ile Gln Ile Gly Leu Ser Ala Val Leu
         330                 335                 340 ctc cca tca gta ttg ctt gct tac atg gga cag gct gca tat ctt cgc   1108
Leu Pro Ser Val Leu Leu Ala Tyr Met Gly Gln Ala Ala Tyr Leu Arg
    345                 350                 355 atc cac cct gaa gat gtt gca gat aca ttc tac aaa tca atc cca ggt   1156
Ile His Pro Glu Asp Val Ala Asp Thr Phe Tyr Lys Ser Ile Pro Gly
360                 365                 370                 375 cca tta tat tgg cca aca ttt gtg gtg gcc gtg gct gct gct ata att   1204
Pro Leu Tyr Trp Pro Thr Phe Val Val Ala Val Ala Ala Ala Ile Ile
             380                 385                 390 gca agc caa gct atg att tct ggt gcc ttt gca atc att gct cag tcc   1252
Ala Ser Gln Ala Met Ile Ser Gly Ala Phe Ala Ile Ile Ala Gln Ser
```

-continued

```
                395                 400                 405
caa gtt ctt ggt tgc ttt cca cgg gtt cgt gtc act cac acc tca aaa     1300
Gln Val Leu Gly Cys Phe Pro Arg Val Arg Val Thr His Thr Ser Lys
        410                 415                 420 aag tat cat ggg cag gtc tac atc cct gag atc aac tat gca tta atg     1348
Lys Tyr His Gly Gln Val Tyr Ile Pro Glu Ile Asn Tyr Ala Leu Met
425                 430                 435 atc tta tgt gta gct gtg aca gct att ttc caa act aca gac aag att     1396
Ile Leu Cys Val Ala Val Thr Ala Ile Phe Gln Thr Thr Asp Lys Ile
440                 445                 450                 455 ggc aat gca tat ggt atc gct gtc gtc ttt gtg atg ttc ata aca aca     1444
Gly Asn Ala Tyr Gly Ile Ala Val Val Phe Val Met Phe Ile Thr Thr
            460                 465                 470 ctt cta gtc aca ctg gta atg gcc atg ata tgg aag aca agt ctg ctg     1492
Leu Leu Val Thr Leu Val Met Ala Met Ile Trp Lys Thr Ser Leu Leu
                475                 480                 485 tgg att gca ctc ttt cca ata ata ttt ggc ggc gca gag ctc gtg tac     1540
Trp Ile Ala Leu Phe Pro Ile Ile Phe Gly Gly Ala Glu Leu Val Tyr
        490                 495                 500 tta tcc tca gca ttc tac aaa ttt gta gaa ggt ggc tac ttg cca cta     1588
Leu Ser Ser Ala Phe Tyr Lys Phe Val Glu Gly Gly Tyr Leu Pro Leu
505                 510                 515 ggt ttt gca gca att ttg atg ctt ata atg ggc aca tgg cac tat gtt     1636
Gly Phe Ala Ala Ile Leu Met Leu Ile Met Gly Thr Trp His Tyr Val
520                 525                 530                 535 cat gtt cat cgg tac aaa tac gag ctc aag aac aaa gtg tca aac aac     1684
His Val His Arg Tyr Lys Tyr Glu Leu Lys Asn Lys Val Ser Asn Asn
            540                 545                 550 tat gtg gca gat ttg gca aca agg aga aat ctt gct agg ttg cca gga     1732
Tyr Val Ala Asp Leu Ala Thr Arg Arg Asn Leu Ala Arg Leu Pro Gly
                555                 560                 565 ata ggc gtt ctg tac tct gag ctt gtg caa gga atc cca ccc ata ctg     1780
Ile Gly Val Leu Tyr Ser Glu Leu Val Gln Gly Ile Pro Pro Ile Leu
        570                 575                 580 ccc cat ttg gta gaa aaa gta cct tcc atc cat tca gtt ctt gtg att     1828
Pro His Leu Val Glu Lys Val Pro Ser Ile His Ser Val Leu Val Ile
585                 590                 595 acc tca ata aag tac tta cca atc agc aat ata gaa aca aat gag cgg     1876
Thr Ser Ile Lys Tyr Leu Pro Ile Ser Asn Ile Glu Thr Asn Glu Arg
600                 605                 610                 615 ttc ctc ttc cga tac gtg gag cca aga gaa tac agg gta ttc cga tgt     1924
Phe Leu Phe Arg Tyr Val Glu Pro Arg Glu Tyr Arg Val Phe Arg Cys
            620                 625                 630 gtg gtg cgc tat ggt tac aac aat aaa gta gaa gat cca aga gag ttc     1972
Val Val Arg Tyr Gly Tyr Asn Asn Lys Val Glu Asp Pro Arg Glu Phe
                635                 640                 645 gag aac ttg ctt att ggg aac ttg aag caa ttc atc cat caa gaa tca     2020
Glu Asn Leu Leu Ile Gly Asn Leu Lys Gln Phe Ile His Gln Glu Ser
        650                 655                 660 ctc tac agc gaa agt agt cat tcc ctt gaa gga gaa gat aat gca ttc     2068
Leu Tyr Ser Glu Ser Ser His Ser Leu Glu Gly Glu Asp Asn Ala Phe
665                 670                 675 gaa gaa tca gga gat gca atg gag cct tct att gaa gtt caa gat gca     2116
Glu Glu Ser Gly Asp Ala Met Glu Pro Ser Ile Glu Val Gln Asp Ala
680                 685                 690                 695 agg ttg ccg aaa agg ttt tta gat gga atc act gct agc cca gtg aac     2164
Arg Leu Pro Lys Arg Phe Leu Asp Gly Ile Thr Ala Ser Pro Val Asn
            700                 705                 710 ggg tta atg gat gag ata gag ttt att cag aga ggg atg gat gat ggt     2212
Gly Leu Met Asp Glu Ile Glu Phe Ile Gln Arg Gly Met Asp Asp Gly
```

```
                      715                 720                 725
gtt gtc cat ctg ctg gga gaa act aat gtg gtg gcg gag caa aat gcc    2260
Val Val His Leu Leu Gly Glu Thr Asn Val Val Ala Glu Gln Asn Ala
            730                 735                 740 ggt ttg gtg aag aaa ata ata gtt gac tac gcc tac aat ttc atg agg    2308
Gly Leu Val Lys Lys Ile Ile Val Asp Tyr Ala Tyr Asn Phe Met Arg
745                 750                 755 aag aac ttc agg caa cca gag aag atc aca tgt gtc cct cat aac agg    2356
Lys Asn Phe Arg Gln Pro Glu Lys Ile Thr Cys Val Pro His Asn Arg
    760                 765                 770                 775 ctg ctg cgg gtg gga atg aca tac gag atc tagagagatg ctcagtggat      2406
Leu Leu Arg Val Gly Met Thr Tyr Glu Ile
                780                 785 tgatcaaatt gacaatagct tcagttttct cagtaccaag tgcagaaagg atatgcagag  2466
gaacagcctc cttgactgaa cagcagagga tggagagatt ttatgcgtac aagtggtgaa  2526
actacagtac atgcaatatg tatttaccat ataatatttt ttttgttagg gaaattctac  2586
tgtataagtg tttgttagca gtaagtatgc atagctgtca aacccctagt ttggccaact  2646
ctttgcctta ttgtggaaaa ctcaaaatct tagtatgtgc agttgtacac aaagattgta  2706
acctaccggc aaaagttaaa caataataa agtatgactt gtgtgccaaa aaaaaaaaa    2766 aaaagagaga gagagagacc gacacgca                                     2794

<210> SEQ ID NO 6
<211> LENGTH: 785
<212> TYPE: PRT
<213> ORGANISM: Triticum aestivum

<400> SEQUENCE: 6

Met Ala Glu Pro Leu Lys Ala Asn Gly Asn Gly Ala Ala Glu Gly Gly
1               5                   10                  15

Ala Ala Gly Ser Ala Phe Ala Ser Val Lys Val Pro Ser Pro Pro
            20                  25                  30

Arg Arg Leu Gln Arg Phe Asp Ser Leu His Met Glu Ala Gly Lys Ile
        35                  40                  45

Pro Gly Gly His Ser Tyr Ala Ala Lys Val Gly Trp Ala Thr Thr Leu
    50                  55                  60

His Leu Ala Phe Gln Ser Leu Gly Val Val Tyr Gly Asp Met Gly Thr
65                  70                  75                  80

Ser Pro Leu Tyr Val Phe Ser Ser Thr Phe Thr Gly Gly Ile Lys Asp
                85                  90                  95

Thr Asp Asp Leu Leu Gly Val Met Ser Leu Ile Ile Tyr Thr Val Leu
            100                 105                 110

Leu Leu Pro Leu Met Lys Tyr Cys Phe Ile Val Leu Arg Ala Asn Asp
        115                 120                 125

Asn Gly Asp Gly Gly Thr Phe Ala Leu Tyr Ser Leu Ile Ser Arg Tyr
    130                 135                 140

Ala Arg Ile Ser Leu Ile Pro Asn Gln Gln Ala Glu Asp Ala Thr Val
145                 150                 155                 160

Ser His Tyr Lys Leu Glu Ser Pro Thr Asn Arg Val Lys Arg Ala His
                165                 170                 175

Trp Ile Lys Glu Lys Met Glu Asn Ser Pro Lys Phe Lys Val Ile Leu
            180                 185                 190

Phe Leu Val Thr Ile Leu Ala Thr Ser Met Val Ile Gly Asp Gly Val
        195                 200                 205

Leu Thr Pro Cys Ile Ser Val Leu Ser Ala Val Thr Gly Ile Lys Gln
```

-continued

```
                210                 215                 220
Ser Ala Lys Ser Leu Thr Gln Gly Gln Ile Ala Gly Ile Ala Ile Gly
225                 230                 235                 240

Ile Leu Ile Ala Leu Phe Leu Val Gln Arg Phe Gly Thr Asp Lys Val
                245                 250                 255

Gly Tyr Thr Phe Gly Pro Val Ile Phe Ile Trp Phe Ile Leu Ile Ala
                260                 265                 270

Gly Ile Gly Ile Tyr Asn Leu Ile Lys His Asp Thr Gly Ile Leu Lys
                275                 280                 285

Ala Phe Asn Pro Gln Tyr Ile Val Glu Tyr Phe Gln Arg Asn Gly Lys
290                 295                 300

Asp Gly Trp Ile Ser Leu Gly Val Ile Leu Cys Ile Thr Gly Thr
305                 310                 315                 320

Glu Ala Met Phe Ala Asp Leu Gly His Phe Asn Val Arg Ala Ile Gln
                325                 330                 335

Ile Gly Leu Ser Ala Val Leu Leu Pro Ser Val Leu Leu Ala Tyr Met
                340                 345                 350

Gly Gln Ala Ala Tyr Leu Arg Ile His Pro Glu Asp Val Ala Asp Thr
                355                 360                 365

Phe Tyr Lys Ser Ile Pro Gly Pro Leu Tyr Trp Pro Thr Phe Val Val
370                 375                 380

Ala Val Ala Ala Ile Ile Ala Ser Gln Ala Met Ile Ser Gly Ala
385                 390                 395                 400

Phe Ala Ile Ile Ala Gln Ser Gln Val Leu Gly Cys Phe Pro Arg Val
                405                 410                 415

Arg Val Thr His Thr Ser Lys Lys Tyr His Gly Gln Val Tyr Ile Pro
                420                 425                 430

Glu Ile Asn Tyr Ala Leu Met Ile Leu Cys Val Ala Val Thr Ala Ile
                435                 440                 445

Phe Gln Thr Thr Asp Lys Ile Gly Asn Ala Tyr Gly Ile Ala Val Val
                450                 455                 460

Phe Val Met Phe Ile Thr Thr Leu Leu Val Thr Leu Val Met Ala Met
465                 470                 475                 480

Ile Trp Lys Thr Ser Leu Leu Trp Ile Ala Leu Phe Pro Ile Ile Phe
                485                 490                 495

Gly Gly Ala Glu Leu Val Tyr Leu Ser Ser Ala Phe Tyr Lys Phe Val
                500                 505                 510

Glu Gly Gly Tyr Leu Pro Leu Gly Phe Ala Ala Ile Leu Met Leu Ile
                515                 520                 525

Met Gly Thr Trp His Tyr Val His Val His Arg Tyr Lys Tyr Glu Leu
530                 535                 540

Lys Asn Lys Val Ser Asn Asn Tyr Val Ala Asp Leu Ala Thr Arg Arg
545                 550                 555                 560

Asn Leu Ala Arg Leu Pro Gly Ile Gly Val Leu Tyr Ser Glu Leu Val
                565                 570                 575

Gln Gly Ile Pro Pro Ile Leu Pro His Leu Val Glu Lys Val Pro Ser
                580                 585                 590

Ile His Ser Val Leu Val Ile Thr Ser Ile Lys Tyr Leu Pro Ile Ser
                595                 600                 605

Asn Ile Glu Thr Asn Glu Arg Phe Leu Phe Arg Tyr Val Glu Pro Arg
                610                 615                 620

Glu Tyr Arg Val Phe Arg Cys Val Val Arg Tyr Gly Tyr Asn Asn Lys
625                 630                 635                 640
```

-continued

```
Val Glu Asp Pro Arg Glu Phe Glu Asn Leu Leu Ile Gly Asn Leu Lys
                645                 650                 655

Gln Phe Ile His Gln Glu Ser Leu Tyr Ser Glu Ser Ser His Ser Leu
        660                 665                 670

Glu Gly Glu Asp Asn Ala Phe Glu Glu Ser Gly Asp Ala Met Glu Pro
    675                 680                 685

Ser Ile Glu Val Gln Asp Ala Arg Leu Pro Lys Arg Phe Leu Asp Gly
    690                 695                 700

Ile Thr Ala Ser Pro Val Asn Gly Leu Met Asp Glu Ile Glu Phe Ile
705                 710                 715                 720

Gln Arg Gly Met Asp Asp Gly Val Val His Leu Leu Gly Glu Thr Asn
                725                 730                 735

Val Val Ala Glu Gln Asn Ala Gly Leu Val Lys Lys Ile Ile Val Asp
                740                 745                 750

Tyr Ala Tyr Asn Phe Met Arg Lys Asn Phe Arg Gln Pro Glu Lys Ile
            755                 760                 765

Thr Cys Val Pro His Asn Arg Leu Leu Arg Val Gly Met Thr Tyr Glu
    770                 775                 780

Ile
785

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
caggaaacag ctatgacc                                                     18

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ctaaagggaa caaaagctg                                                    19

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
tgtaaaacga cggccagt                                                     18

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
ctgaagccgg tttggagtga tcgtc                                             25

<210> SEQ ID NO 11
```

```
<211> LENGTH: 28
<212> TYPE: DNA
<213> ORGANISM: Artificial Sequence
<220> FEATURE:
<223> OTHER INFORMATION: Primer RC523

<400> SEQUENCE: 11
ggagggtggt gacgatcatg accatcac                                          28

<210> SEQ ID NO 12
<211> LENGTH: 26
<212> TYPE: DNA
<213> ORGANISM: Artificial Sequence
<220> FEATURE:
<223> OTHER INFORMATION: Primer RC738

<400> SEQUENCE: 12
ccagctgtga cgcagaggca gagaac                                            26

<210> SEQ ID NO 13
<211> LENGTH: 25
<212> TYPE: DNA
<213> ORGANISM: Artificial Sequence
<220> FEATURE:
<223> OTHER INFORMATION: Primer RC756

<400> SEQUENCE: 13
accagcggca cccagcctcc ttgag                                             25

<210> SEQ ID NO 14
<211> LENGTH: 26
<212> TYPE: DNA
<213> ORGANISM: Artificial Sequence
<220> FEATURE:
<223> OTHER INFORMATION: Primer RC757

<400> SEQUENCE: 14
aggcaaggag gaagtgcttc cgccaa                                            26

<210> SEQ ID NO 15
<211> LENGTH: 32
<212> TYPE: DNA
<213> ORGANISM: Artificial Sequence
<220> FEATURE:
<223> OTHER INFORMATION: Primer RC856

<400> SEQUENCE: 15
atcccgggcg attgcctgct ctgaatgatc ag                                     32

<210> SEQ ID NO 16
<211> LENGTH: 34
<212> TYPE: DNA
<213> ORGANISM: Artificial Sequence
<220> FEATURE:
<223> OTHER INFORMATION: Primer RC857

<400> SEQUENCE: 16
gcgttaacgt cgccctgtac aaaactcaga ccca                                   34
```